(12) United States Patent
Franco De Sarabia Rosado et al.

(10) Patent No.: US 7,919,294 B2
(45) Date of Patent: Apr. 5, 2011

(54) PROCESS FOR PREPARING STABILIZED REACTION MIXTURES WHICH ARE PARTIALLY DRIED, COMPRISING AT LEAST ONE ENZYME, REACTION MIXTURES AND KITS CONTAINING SAID MIXTURES

(75) Inventors: Pedro Manuel Franco De Sarabia Rosado, Madrid (ES); Gemma Limones Lopez, Madrid (ES); Antonio Madejon Seiz, Madrid (ES); Maria Dolores Marin Alberdi, Madrid (ES)

(73) Assignee: Biotools Biotechnological & Medical Laboratories, S.A., Madrid (ES)

( * ) Notice: Subject to any disclaimer, the term of this patent is extended or adjusted under 35 U.S.C. 154(b) by 1182 days.

(21) Appl. No.: 10/292,848

(22) Filed: Nov. 12, 2002

(65) Prior Publication Data
US 2003/0119042 A1 Jun. 26, 2003

Related U.S. Application Data

(63) Continuation of application No. PCT/ES02/00109, filed on Mar. 11, 2002.

(30) Foreign Application Priority Data

Mar. 12, 2001 (ES) .................... 200100569

(51) Int. Cl.
*C12N 9/96* (2006.01)
(52) U.S. Cl. ............ 435/188; 435/183; 435/6; 435/91.2; 435/195; 435/975; 536/1.11
(58) Field of Classification Search .................. 435/177, 435/178, 184, 188, 180, 183, 195, 6, 91.2; 536/1.11
See application file for complete search history.

(56) References Cited

U.S. PATENT DOCUMENTS

| | | | |
|---|---|---|---|
| 2,992,237 A * | 7/1961 | Dieckelmann | 549/531 |
| 3,622,462 A * | 11/1971 | Delin et al. | 435/230 |
| 3,892,876 A * | 7/1975 | Hobday et al. | 426/576 |
| 5,556,771 A | 9/1996 | Shen et al. | |
| 5,565,318 A * | 10/1996 | Walker et al. | 435/4 |
| 5,614,387 A | 3/1997 | Shen et al. | |
| 5,876,992 A * | 3/1999 | De Rosier et al. | 435/188 |
| 5,925,520 A * | 7/1999 | Tully et al. | 435/6 |
| 5,955,448 A * | 9/1999 | Colaco et al. | 514/53 |
| 6,136,578 A * | 10/2000 | Sørensen et al. | 435/188 |
| 6,150,094 A * | 11/2000 | Maier et al. | 435/6 |
| 6,300,073 B1 * | 10/2001 | Zhao et al. | 435/6 |
| 6,436,897 B2 * | 8/2002 | Danko et al. | 514/2 |
| 6,964,771 B1 * | 11/2005 | Roser et al. | 424/400 |
| 2002/0012687 A1 * | 1/2002 | Roser et al. | 424/423 |

FOREIGN PATENT DOCUMENTS

WO WO 93/00807 A1 1/1993
WO WO 00/34444 A2 6/2000

OTHER PUBLICATIONS

Carpenter et al. "Optimization of storage stability of lyophilized actin using combinations of disaccharides and dextran" J. Pharm. Sci. (2000) 89(2): 199-214.*
Minton, A. "The influence of macromolecular crowding and macromolecular confinement on biochemical reactions in physiological media," J. Biol. Chem. (2001) 276(14): 10577-10580.*
Harrison et al. "Stabilization of T4 polynucleotide kinase by macromolecular crowding" Nucleic Acids Res. (1986) 14(4): 1863-1870.*
Webster's II New Riverside Univeristy Dictionary (1994) (Moughton-Mifflin: Boston, MA) p. 120.*

* cited by examiner

*Primary Examiner* — Sandra Saucier
*Assistant Examiner* — Susan Hanley
(74) *Attorney, Agent, or Firm* — Sughrue Mion, PLLC

(57) ABSTRACT

The invention relates to a method consisting of bringing into contact, in one container, (a) an aqueous solution of a reaction mixture comprising at least one enzyme, and (b) an aqueous solution of a stabilizing mixture comprising (i) at least one protective agent against drying, (ii) at least one inhibitor of the condensation reaction between carbonyl or carboxyl groups and amine or phosphate groups, and (iii) at least one inert polymer capable of generating a mesh structure preventing the mobility of the dried reagents. The invention also consists of removing all or part of the water contained in the resulting aqueous solution. Said process is suitable for carrying out enzymatic reactions, for example, amplifying, sequencing and characterizing nucleic acids, performing hybridization tests and for the restriction analysis.

19 Claims, No Drawings

SEQUENCE LISTING

<160> NUMBER OF SEQ ID NOS: 19

<210> SEQ ID NO 1
<211> LENGTH: 23
<212> TYPE: DNA
<213> ORGANISM: Artificial sequence
<220> FEATURE:
<223> OTHER INFORMATION: I-1 oligonucleotide primer

<400> SEQUENCE: 1
ccatccatct cagcatgatg aaa                                              23

<210> SEQ ID NO 2
<211> LENGTH: 26
<212> TYPE: DNA
<213> ORGANISM: Artificial sequence
<220> FEATURE:
<223> OTHER INFORMATION: I-2 oligonucleotide primer

<400> SEQUENCE: 2
gcccctcaga atgatatttg tcctca                                           26

<210> SEQ ID NO 3
<211> LENGTH: 20
<212> TYPE: DNA
<213> ORGANISM: Artificial sequence
<220> FEATURE:
<223> OTHER INFORMATION: II-1 oligonucleotide primer

<400> SEQUENCE: 3
caaggatgct cttggctctt                                                  20

<210> SEQ ID NO 4
<211> LENGTH: 20

```
<212> TYPE: DNA
<213> ORGANISM: Artificial sequence
<220> FEATURE:
<223> OTHER INFORMATION: II-2 oligonucleotide primer

<400> SEQUENCE: 4
gtggtagcag atgagagtga                                               20

<210> SEQ ID NO 5
<211> LENGTH: 22
<212> TYPE: DNA
<213> ORGANISM: Artificial sequence
<220> FEATURE:
<223> OTHER INFORMATION: H1 oligonucleotide primer

<400> SEQUENCE: 5
gcataaggaa tgcaaagaac ag                                            22

<210> SEQ ID NO 6
<211> LENGTH: 19
<212> TYPE: DNA
<213> ORGANISM: Artificial sequence
<220> FEATURE:
<223> OTHER INFORMATION: H2 oligonucleotide primer

<400> SEQUENCE: 6
aggacttcca agccgaagc                                                19

<210> SEQ ID NO 7
<211> LENGTH: 22
<212> TYPE: DNA
<213> ORGANISM: Artificial sequence
<220> FEATURE:
<223> OTHER INFORMATION: P1 oligonucleotide primer

<400> SEQUENCE: 7
agtgtgtatc caatcgagtt tc                                            22

<210> SEQ ID NO 8
<211> LENGTH: 21
<212> TYPE: DNA
<213> ORGANISM: Artificial sequence
<220> FEATURE:
<223> OTHER INFORMATION: P2 oligonucleotide primer

<400> SEQUENCE: 8
cgcagttgct tgtctccaga a                                             21

<210> SEQ ID NO 9
<211> LENGTH: 18
<212> TYPE: DNA
<213> ORGANISM: Artificial sequence
<220> FEATURE:
<223> OTHER INFORMATION: F oligonucleotide primer

<400> SEQUENCE: 9
gagccgcctg gataccgc                                                 18

<210> SEQ ID NO 10
<211> LENGTH: 21
<212> TYPE: DNA
<213> ORGANISM: Artificial sequence
<220> FEATURE:
<223> OTHER INFORMATION: M oligonucleotide primer

<400> SEQUENCE: 10
cgctctggtc cgtcttgcgc c                                             21
```

<210> SEQ ID NO 11
<211> LENGTH: 21
<212> TYPE: DNA
<213> ORGANISM: Artificial sequence
<220> FEATURE:
<223> OTHER INFORMATION: O oligonucleotide primer

<400> SEQUENCE: 11
agttccccta gaatagttac a                                              21

<210> SEQ ID NO 12
<211> LENGTH: 19
<212> TYPE: DNA
<213> ORGANISM: Artificial sequence
<220> FEATURE:
<223> OTHER INFORMATION: V oligonucleotide primer

<400> SEQUENCE: 12
gccctccaat tgccttctg                                                 19

<210> SEQ ID NO 13
<211> LENGTH: 21
<212> TYPE: DNA
<213> ORGANISM: Artificial sequence
<220> FEATURE:
<223> OTHER INFORMATION: EV1M oligonucleotide primer

<400> SEQUENCE: 13
acccaaagta gtcggttccg c                                              21

<210> SEQ ID NO 14
<211> LENGTH: 19
<212> TYPE: DNA
<213> ORGANISM: Artificial sequence
<220> FEATURE:
<223> OTHER INFORMATION: EV2P oligonucleotide primer

<400> SEQUENCE: 14
caagcacttc tgtttcccc                                                 19

<210> SEQ ID NO 15
<211> LENGTH: 21
<212> TYPE: DNA
<213> ORGANISM: Artificial sequence
<220> FEATURE:
<223> OTHER INFORMATION: EV1P oligonucleotide primer

<400> SEQUENCE: 15
cggtaccttt gtrcgcctgt t                                              21

<210> SEQ ID NO 16
<211> LENGTH: 20
<212> TYPE: DNA
<213> ORGANISM: Artificial sequence
<220> FEATURE:
<223> OTHER INFORMATION: VI-1 oligonucleotide primer

<400> SEQUENCE: 16
gcmcagggwc ataayaatgg                                                20

<210> SEQ ID NO 17
<211> LENGTH: 20
<212> TYPE: DNA
<213> ORGANISM: Artificial sequence
<220> FEATURE:
<223> OTHER INFORMATION: VI-2 oligonucleotide primer

```
-continued

<400> SEQUENCE: 17
cgtccmarrg gawactgatc                                              20

<210> SEQ ID NO 18
<211> LENGTH: 20
<212> TYPE: DNA
<213> ORGANISM: Artificial sequence
<220> FEATURE:
<223> OTHER INFORMATION: VI-3 oligonucleotide primer

<400> SEQUENCE: 18
tgtcaaaaac cgttgtgtcc                                              20

<210> SEQ ID NO 19
<211> LENGTH: 20
<212> TYPE: DNA
<213> ORGANISM: Artificial sequence
<220> FEATURE:
<223> OTHER INFORMATION: VI-4 oligonucleotide primer

<400> SEQUENCE: 19
gagctgtcgc ttaattgctc                                              20
```

PROCESS FOR PREPARING STABILIZED REACTION MIXTURES WHICH ARE PARTIALLY DRIED, COMPRISING AT LEAST ONE ENZYME, REACTION MIXTURES AND KITS CONTAINING SAID MIXTURES

CROSS-REFERENCE TO RELATED APPLICATIONS

This application is a continuation of International Application No. PCT/ES02/00109, filed Mar. 11, 2002, which claims priority to Spanish Application No. P200100569, filed Mar. 12, 2001, the disclosures of which are herein incorporated by reference.

BACKGROUND OF THE INVENTION

The invention relates to the preparation of stabilized reaction mixtures, which are totally or partially dried, comprising at least one enzyme, by means of adding a stabilizing mixture to a solution containing the reaction mixture, and the subsequent removal of all or part of the water present in the resulting solution, as well as to the resulting reaction mixtures and to kits comprising said reaction mixtures.

BRIEF SUMMARY OF THE INVENTION

Deoxyribonucleic acids (DNA) and ribonucleic acids (RNA) are long, linear macromolecules which are responsible for storing and transmitting genetic information. They have monomeric units called nucleotides, each one of which is formed by a nitrogenous, purine or pyrimidine base, a simple sugar (deoxyribose in the case of DNA and ribose in the case of RNA), and an inorganic phosphate. The nucleotides in a nucleic acid are bonded together by means of phosphodiester bonds through the sugar of adjacent nucleotides. The nitrogenous bases are covalently bonded to the sugar-phosphate skeleton. Every nucleic acid mainly has four different nitrogenous bases, two pyrimidine bases and two purine bases. The purine bases are the same for both DNA and RNA, both containing adenine (A) and guanine (G). With regard to the pyrimidine bases, both nucleic acids contain cytosine (C), thymine (T) being DNA specific and uracil (U) RNA specific. The sequence of these nitrogenous bases determines the genetic information carried by nucleic acids, as well as their three-dimensional shape. While RNA is generally found in nature as a single polynucleotide chain, DNA is normally found as a double polynucleotide chain wherein both strands are arranged in an anti-parallel manner, associated by hydrogen bonds formed between a purine base and a pyrimidine base which are complementary to one another.

Nucleic acid amplification is the most widely used tool for precisely identifying a determined nucleic acid, consisting of the exponential multiplication of the initial amount of a specific or characteristic segment of nucleic acid. That amplified segment can be used in subsequent applications such as cloning and restriction analysis. Sequencing nucleic acids consists of determining the nucleotide sequence of a determined nucleic acid fragment. Nucleic acid amplification and sequencing, as well as fragment restriction analysis, a technique consisting of identifying or characterizing a nucleic acid on the basis of the differential sizes caused by endonuclease enzymes called restriction enzymes, are widely used techniques, among other possible uses, in biomedical research, in medical and veterinary diagnosis of infectious and hereditary diseases, in human and animal genetic analysis, in food analysis, in environmental control, and in forensic and criminological analysis.

There are several methods for in vitro nucleic acid synthesis and amplification. The best known and used is the polymerase chain reaction, commonly referred to by its English abbreviation, PCR (Saiki et al., Science, 230, 1350-1354 (1985), Mullis et al., U.S. Pat. Nos. 4,683,195, 4,683,202 and 4,800,159). In its simplest form, PCR consists of a cyclical DNA amplification process through which one or more specific DNA sequences contained in a nucleic acid or in a mixture of nucleic acids is exponentially amplified by using two oligonucleotide primers which, due to the complementarity of bases, specifically bind to two facing regions of the problem DNA previously denatured by heat. Each one of the problem DNA strands to which its corresponding primer has bound can be copied to the complementary DNA form by means of the action of a DNA polymerase activity, using the oligonucleotide as a primer of the polymerization reaction. By successive repetitive cycles of this process an exponential enrichment of the problem DNA fragment comprised between the hybridization points of the oligonucleotides is obtained. Using thermostable DNA polymerases permits carrying out successive denaturation cycles, annealing the oligonucleotide to the DNA substrate and elongating the chain, without adding new polymerase activity in each cycle. In the case of analyzing the presence of a DNA with a relative abundance, this process is sufficient for its identification. Nonetheless, it is frequent to analyze samples wherein the abundance of the problem DNA is below the limits of a simple PCR. The nested-PCR technique has been developed for analyzing these samples. Two coupled amplification processes are carried out in this system, the second of which uses the amplified product of a first PCR as a substrate. In order to increase the process specificity, the oligonucleotides used in the second amplification reaction are different from those used in the first and they hybridize with inner areas of the product of the first amplification.

Given that the amplification reaction uses DNA polymerase activities which require DNA molecules as a substrate, the direct analysis of RNA molecules requires a prior reverse transcription (RT) step by means of which a copy DNA (cDNA) molecule is synthesized which is complementary to the problem RNA. Then, the cDNA thus obtained can be used as an amplification reaction substrate (Mocharla et al., Gene 93:271-275 (1990)). The amplification system used could be a simple reaction (RT-PCR) or a nested amplification (RT-nested PCR), depending on the relative abundance of the original RNA substrate. The development of DNA polymerase activities modified with reverse transcriptase activities permits carrying out the RT-amplification process by using a single enzymatic activity in highly astringent conditions.

The previously described cyclical nucleic acid amplification methods use thermostable polymerase enzymes, obtained from different thermophilic microorganisms such as *Thermus aquaticus* (Kaledin et al., Biokhimiya 45, 644-651 (1980); Chien et al., J. Bacteriol. 127:1550-1557 (1976); U.S. Pat. No. 4,889,818), and *Thermus thermophilus* ("Tth"; Ruttimann et al., Eur. J. Biochem. 149:41-46 (1985)), among others. Several of these thermostable DNA polymerase enzymes, for example that which comes from *T. aquaticus*, (Jones et al., Nucleic Acids Research 17:8387-8388 (1989)), as well as some mesophilic DNA polymerase enzymes such as the DNA polymerase I of *Escherichia coli* (Karkas et al., Proc. Natl. Acad. Sci. U.S.A. 70:3834-3838 (1973); Leob et al., Nature New Biol. 242:66-69 (1973)) exhibit a double enzymatic activity, DNA polymerase and reverse transcriptase, depending on the cofactor which is present in the reaction mixture, such that in the presence of magnesium ion, DNA polymerase activity is exhibited, whereas in the presence of manganese ion, reverse transcriptase activity is exhibited.

Unlike mesophilic proteins, thermostable enzymes do not denature with heat, but rather they require high temperatures for carrying out their activity. This is mainly due to the modifications in their amino acid sequence, which are transferred to their global protein folding or tertiary structure. These are not drastic modifications, but rather thermostability arises as a consequence of the sum of small enthalpic and entropic-type interactions forming a synergic contribution to obtaining a more rigid and heat resistant tertiary structure. The amino acid changes stand out among these modifications, which lead to a more rigid tertiary structure (Menéndez-Arias and Argos, J. Mol. Biol., 206:397-406 (1989)) or the elimination of the residues which are sensitive to degradation due to deamination (Asn, Gln) or oxidation (Met, Cys), especially in the more sensitive areas of the protein, such as the loops (Watanabe et al., J. Biol. Chem., 266:24287-24294 (1991)). Hydrogen bridge formation and the extensive network formation between them, between the amino acids of the protein as well as with water molecules of the medium (Pace et al., FASEB J., 10:75-83 (1996)), is another of the modifications leading to thermostability, as well as saline bridge formation between charged surface residues, or as a manner of neutralizing the polar residues remaining in the hydrophobic interior of the protein (Yip et al., Structure, 3:1147-1158 (1995)). Other modifications of this type are the formation of secondary structures, especially α-helices by means of stabilizing their inner dipole (Rentier-Delrue et al., J. Mol. Biol., 229: 85-93)) and the formation of hydrogen bonds (Warren and Petsko, Prot. Eng., 8:905-913 (1995)), as well as increasing the packaging in the hydrophobic interior, i.e. making the protein more compact (Matthews, FASEB J., 10: 35-41 (1996)). By the aforementioned, it is evident that preserving the tertiary structure of the thermostable enzymes, and consequently their activity and functionality passes through preserving the integrity of the interactions of the protein with the aqueous molecules surrounding it, even more so than the non-thermostable mesophilic enzymes.

It is well known that products such as gelatin, bovine serum albumin (BSA), ammonium sulfate and THESIT™ dodecylpoly(ethyleneglycolether)$_9$ non-ionic surfactant, among others, stabilize polymerase enzymes and dNTPs, and the non-ionic surfactants such as NP40™ octylphenolpoly(ethyleneglycolether)$_8$ non-ionic surfactant and TWEEN™ 20 poly(oxytheylene)-sorbitan-monolaurate non-ionic surfactant improve nucleic acid amplification reactions (Saiki et al., Science 239:487-491 (1988)).

Restriction enzymes are endonuclease enzymes that break the phosphodiester bonds within the DNA double chain. One type of these restriction enzymes, called type II, have the property of recognizing a determined DNA nucleotide sequence, causing the bonds which join the nucleotides together within that determined sequence to break, consequently cutting a single DNA into precise and reproducible fragments, generating what is called a restriction map. Type II enzymes are widely used in various molecular biology techniques, such as cloning, identifying specific DNA sequences and fragments, and analyzing restriction maps, among others (Molecular Cloning: A Laboratory Manual, J. Sambrook et al., 2nd Ed. 1989).

The activity of enzymes and other biological macromolecules, including antigens and antibodies, quite often depends mainly on its three-dimensional shape, called a tertiary structure, such that if this three-dimensional shape is modified by any factor, the biological activity or functionality of the macromolecule may be reduced or even disappear. Water forms a protective wrapping around the biological macromolecules, stabilizing the tertiary structure of the macromolecules by means of hydrophobic/hydrophilic interactions. These interactions also block the reagent chemical groups which can be found on the macromolecule surface. Upon removing this protective aqueous wrapping, which, for example, occurs in any drying process, distortions may occur in the tertiary structure of the macromolecules, it thereby being modified, and the reagent chemical groups (amine, phosphate, carboxyl groups, etc.) are thereby free to react with one another or with other reagent groups of other close-by macromolecules, thus being able to contribute to the loss of the original tertiary structure and even forming aggregates between various macromolecules which are similar to or different from one another, which also generally implies the decrease or even loss of the biological activity or functionality of the macromolecules, as well as modifications in their tertiary structures. These reactions between peripheral reagent chemical groups may even occur once the macromolecules are suitably dried due to the plasticity of the mediums in which they are located, a reason for which a decrease in the biological activity or functionality of the dried macromolecules can be seen when time has elapsed. As a consequence, it is highly important to substitute the aqueous wrapping surrounding the macromolecules with protective agents that efficiently substitute the water molecules in their function of maintaining the tertiary structures of the macromolecules and in their function of stabilizing and protecting the surface reagent groups.

The habitual method for conserving and transporting the aforementioned DNA polymerase enzymes and restriction enzymes, as well as other enzymes used in molecular biology and for the aforementioned uses, comprises freezing them at −20° C., stabilizing them to withstand these low temperatures mainly by means of adding glycerol to their aqueous form. This method preserves the enzyme activity for several months with hardly any loss of activity as long as the conservation temperature does not raise above −20° C., it thereby being vitally important to preserve the cold chain, important losses of enzyme activity or inactivity being recorded if this cold chain is interrupted for several hours. Even when using this transportation and conservation method by means of freezing at −20° C., it is not advisable to ship and conserve all the reaction components in a single container, vial or tube since undesirable chemical or biochemical reactions between the different components could cause their inactivation or the generation of artifacts which could interfere or mask the interpretation of the experimental results. It can be deduced from the aforementioned that it would be very economically convenient to have a system which made it possible to conserve and transport said macromolecules at room temperature, thus being able to prevent the necessary cold chain preservation, particularly if this conservation system permitted dispatching to the market all the elements (enzymes, cofactors, additives, etc.) which are necessary for carrying out the desired enzymatic reaction in a single container.

In nucleic acid amplification by means of the previously described techniques, each one of the components intervening in the reaction, i.e., the DNA polymerase enzyme, the reaction buffer containing reaction enhancing additives or stabilizers, magnesium chloride, or manganese chloride in the case of RT, the oligonucleotides used as reaction primers, the deoxyribonucleotides (dATP, dCTP, dGTP and dTTP), and the sample containing the nucleic acid to be amplified, are separated, conserved by means of freezing as previously explained, and they must be mixed prior to carrying out the reaction, being necessary to add and mix very small amounts (microliters) of each one of them, with frequent errors occurring in dosing and pipetting each one of said reagents, which ends up generating uncertainty as to the reproducibility of the results obtained by means of applying these techniques, an especially preoccupying uncertainty in the case of human diagnosis. This variability due to the possibility of an error in pipetting the different reagents to be added to the amplification reaction also affects the sensitivity of the technique, which generates a new uncertainty as to applying these techniques in diagnosing diseases in humans, and especially in determining infection levels and gene expression levels.

Furthermore, while pipetting and adding the sample to be analyzed to the reaction mixture, aerosols are produced which frequently cause cross-contaminations between samples to be analyzed (Kwok, S. et al., Nature, 339:237-238 (1989)), thus generating false positive results, which are also very important in the case of human diagnosis.

Various techniques have been described and used for preserving by means of drying biological macromolecules, and their use and applicability are conditioned by their capacity to preserve the functional features of the product to which it is applied.

Of the techniques described, lyophilization is the main preservation technique by means of drying, and it is a method in which the elimination of water is achieved by means of freezing the wet product and the subsequent sublimation of ice in low pressure conditions. Sublimation is the process through which a solid evaporates without passing through the liquid state, thus the previously indicated term low pressure refers to a gas pressure value which is lower than the triple point of water, a gas pressure in which water coexists in the solid, liquid and gaseous states. In order to perform lyophilization, the solution or product to lyophilize must be completely frozen at a temperature and speed depending on the type of material to be lyophilized. The necessary lyophilizing equipment is expensive, and the lyophilization process is relatively slow, therefore these economic factors quite often dissuade its use. Other drying systems are well known, such as drying on a fluidized bed, drying at room temperature and atmospheric pressure, drying at room temperature and reduced pressure, drying at a high temperature and atmospheric pressure, drying at a high temperature and reduced pressure. Choosing the drying method to use depends on its degree of efficiency, on its more or less aggressiveness against the composition to be preserved by means of drying, and on economic factors.

Different solutions have been proposed for preserving the integrity of the biological macromolecules during the drying process, as well as for stabilizing and preserving the functionality of the dried elements during the conservation and storage process.

In Cryobiology 19:306-316 (1982), Clegg et al. describe the protective effect of glycerol and trehalose on the cellular response to drying.

In Cryobiology 20:346-356 (1983), in Archives Biochem. Biophysics 232:400-497 (1984) and in Biochimica et Biophysica Acta 769:141-150 (1984), Crowe et al. describe the action of various carbohydrates on the stabilization of cellular membranes, indicating the protective effect which is significantly greater than the non-reducing disaccharide known as trehalose (α-D-glucopyranosyl-α-D-glucopyranoside) in drying cellular organelles.

Carpenter et al. (Cryobiology 24:455-464 (1987)) indicate that the maltose, sucrose, lactose and trehalose disaccharides increase the stability of the activity of a purified preparation of the phosphofructokinase enzyme after its drying.

European patent application number EP 140489, belonging to Wako Pure Chemical Industries, discloses a process for protecting an immunoactive protein (an antibody) on a carrier (for example, a glass bead) against drying at room temperature by means of immersing it in a sugary solution, optionally together with a protein such as bovine serum albumin. A significant number of sugars are mentioned (ribose, glucose, fructose, mannose, galactose, maltose, sucrose, lactose, as well as other oligosaccharides and polysaccharides), those preferred being lactose, sucrose and dextrin solutions based on their greater protective effect.

U.S. Pat. No. 4,891,319, granted to Quadrant Bioresources Limited, discloses the use of trehalose as a protective agent against drying of proteins, antibodies and other biological macromolecules.

In Chemical Abstracts 95:517 (1981), O. Tooru et al. describe the protective effect of sugars and alkoxylic sugars against denaturing and drying muscular fibers in fish.

Patent application number EP 91258 discloses a method for stabilizing the tumor necrosis factor (TNF) by means of storing or lyophilizing the purified TNF protein in the presence of a stabilizing protein such as bovine serum albumin or gelatin.

Patent application number WO 91/18091, belonging to Quadrant Holdings Cambridge Limited, discloses a method for preserving biological substances in a dried state by means of using non-reducing glycosides that come from polyhydroxylated compounds (preferably sorbitol or mannitol), such as maltitol, lactitol, and both palatinitol isomers, and a non-reducing oligosaccharide such as raffinose, stachyose and melezitose.

In J. Jpn. Diabetes Soc, 34:403-407 (1991), Igaki et al. indicate L-lysine to be an inhibitor of the condensation reactions between amine and carbonyl groups located in the periphery of biological macromolecules.

U.S. Pat. No. 5,955,448, granted to Quadrant Holdings Cambridge Limited, claims a method of stabilizing samples and biological macromolecules, including endonuclease restriction enzymes, dried by means of adding non-reducing carbohydrates and an inhibitor of the condensation reactions between peripheral amine and carbonyl groups. Stabilizing recombinant β-interferon is also known by means of using a stabilizing agent such as a detergent or glycerol, it also being able to contain other proteins, sucrose, trehalose and other polyhydroxyl derivatives of the carbohydrates as additional stabilizing agents, especially dextrose.

Other references on drying and preservation methods against drying of the biological macromolecules can be found in Pikal M. J., BioPharm 3:18-20, 22-23, 26-27 (1990), Carpenter et al., Cryobiology 25: 459-470 (1988), Roser B., BioPharm 4:47-53, (1991), Colaco et al., Bio/Technol. 10:1007-1011 (1992), and Carpenter et al., Cryobiology 25:244-255 (1988).

On the other hand, U.S. Pat. No. 5,861,251, granted to Bioneer Corporation, claims a process for preparing a ready-to-use reagent dried by means of lyophilization for DNA amplification by means of adding glucose or sorbitol as preservatives to a reaction mixture containing all the components which are necessary for carrying out the reaction, i.e., a thermostable DNA polymerase enzyme, a reaction buffer containing all the components which are necessary for carrying out the reaction, and the necessary deoxynucleotide triphosphates or dideoxynucleotide triphosphates as substrates of the polymerization reaction, plus a water soluble dye, not mentioning the addition of oligonucleotide probes or primers to the ready-to-use reagent.

U.S. Pat. No. 5,614,387, granted to Gen-Probe Incorporated, discloses a ready-to-use reagent dried by means of lyophilization for RNA amplification by means of adding a non-reducing disaccharide, preferably trehalose or sucrose, and/or polyvinylpyrrolidone as preservatives to a reaction mixture containing all the reagents which are necessary for carrying out the nucleic acid amplification, including an RNA polymerase and/or a reverse transcriptase, not mentioning in the examples any thermostable enzyme, together with a reaction buffer containing all the components which are necessary for carrying out the reaction, and the deoxynucleotide triphosphates or dideoxynucleotide triphosphates which are necessary as substrates of the polymerization reaction, plus a water soluble dye.

U.S. Pat. No. 5,935,834, granted to Asahi Kasei Kogyo Kabushiki Kaisha, claims a ready-to-use reagent which is obtainable by means of drying and preserving in the presence of trehalose and containing all the elements which are necessary for carrying out a reverse transcription of the RNA which comes from a virus.

Although various solutions have been proposed for preserving the integrity of biological macromolecules during the drying process, as well as for stabilizing and preserving the functionality of the dried elements during the conservation and storage process, there is still a need to develop alternative solutions that increase the potential of means in order to satisfy such purposes. The present invention provides a solution to said need.

DETAILED DESCRIPTION OF THE INVENTION

The invention provides a process for preparing a stabilized and totally or partially dried reaction mixture, said mixture comprising at least one enzyme, heretofore process of the invention, which comprises;
  a) bringing into contact in a single container:
    i) an aqueous solution of a reaction mixture comprising at least one enzyme; and
    ii) an aqueous solution of a stabilizing mixture composed of:
      at least one protective agent against drying;
      at least one inhibitor of the condensation reaction between carbonyl or carboxyl groups and amine or phosphate groups; and
      at least one inert polymer capable of generating a mesh structure preventing the mobility of the dried reagents;
  in order to obtain an aqueous solution comprising said reaction mixture together with said stabilizing mixture; and
  b) removing all or part of the water contained in said aqueous solution obtained in step a), until obtaining a totally or partially dried mixture comprising said enzyme and said stabilizing mixture and has a moisture content which is equal to or less than 30%, in order to obtain a stabilized reaction mixture which is totally or partially dried, comprising at least one enzyme.

The reaction mixture comprises one or more enzymes intervening in one or several enzymatic reactions together with all or part of the reagents which are necessary for carrying out the enzymatic reactions in which said enzymes intervene. In a particular embodiment, the reaction mixture contains all the reagents which are necessary for carrying out the reaction or reactions in which the enzyme(s) present in the reaction mixture intervenes, mixed in suitable amounts in said container, such as a reaction tube or a well of a multi-well plate, in which the enzymatic reaction to be performed will be subsequently carried out after rehydrating and adding the substrate or problem sample.

The enzyme or enzymes present in the reaction mixture can be any enzyme. In a particular embodiment, said enzyme is selected from the group formed by both thermostable and thermolabile nucleic acid amplification enzymes, from both RNA and DNA nucleic acids, restriction enzymes, enzymes intervening in nucleic acid amplification, sequencing or characterization reactions, and mixtures thereof. Therefore, in a particular embodiment, the reaction mixture comprises an enzyme selected from nucleic acid amplification enzymes, restriction enzymes, enzymes intervening in nucleic acid amplification, sequencing or characterization reactions, and mixtures thereof, together with all the reagents which are necessary for carrying out the reactions in which the aforementioned enzymes intervene, and including cofactors, enzyme substrates and other additives which enhance the enzymatic reactions, it also being possible to optionally include labeled or unlabeled oligonucleotide primers and probes for carrying out a specific amplification, for example, detecting a determined pathogen or genetic mutation in a sample.

The aqueous solution of the reaction mixture can be prepared outside of the container and subsequently added to it as it is, or it can be directly formed in the container by means of adding and mixing the different reaction mixture components in the container itself.

The stabilizing mixture is composed of (i) at least one protective agent against drying, (ii) at least one inhibitor of the condensation reaction between carbonyl or carboxyl groups and amine or phosphate groups; and (iii) at least one inert polymer which, when dried, generates a mesh structure preventing the mobility of the dried reagents.

The protective agent against drying has the main task of stabilizing the tertiary structure of the enzymes and nucleotides optionally present in the reaction mixture during the drying process, in this purpose substituting the water molecules forming the protective wrapping in the aqueous solution that helps to maintain the three-dimensional structure of the macromolecules, furthermore blocking the reactions that could occur between the reagent chemical groups that may exist on the surface of the macromolecules, they thereby also have a stabilizing effect on the long term conservation of the dried mixtures. The protective agent against drying can be a suitable, non-reducing carbohydrate, particularly a non-reducing disaccharide or trisaccharide, or a mixture of said compounds. In a particular embodiment, the protective agent against drying is selected from among the non-reducing disaccharides, palatinitol (6-α-D-glucopyranosyl-mannitol) and trehalose, the non-reducing trisaccharides, raffinose and melezitose, and mixtures thereof. Other non-reducing carbohydrates, such as sucrose, have been proven effective in drying enzymes, but not so in drying both enzymes and oligonucleotides.

Several non-reducing compounds from the polyalcohol group, such as sorbitol and glycerol, have been assayed as protective agents against drying and as stabilizers of the dried mixtures during their storage. Both are proven to be relatively effective in their independent use as agents for protecting the enzymes during the drying process and in their subsequent conservation, especially sorbitol. In the drying process of reaction mixtures containing both enzymes and oligonucleotides, together with the stabilizing mixture containing non-reducing carbohydrates, inhibitors of the condensation reactions and inert polymers, it can be seen that whereas glycerol exhibits a beneficial protective effect in all the cases in conjunction with the stabilizing mixture components, especially in conjunction with the non-reducing carbohydrates melezitose, palatinitol, trehalose and sucrose, sorbitol does not exhibit any beneficial effect, but rather, on the contrary, it inhibits the protective effect of said elements. The use of sorbitol as a protective agent against drying and as a stabilizer during the conservation of the reaction mixtures is effective when no oligonucleotides are present in those reaction mixtures, exhibiting no protective or stabilizing action when oligonucleotide chains are present in these mixtures. Therefore, apart from one or several non-reducing carbohydrates, the stabilizing mixture may optionally contain glycerol as a protective agent against drying.

The inhibitor of the condensation reactions has the purpose of inhibiting the condensation reactions which may occur between the carboxyl, carbonyl, amine and phosphate groups which are on the surface of the macromolecules present in the reaction mixture to be dried, so that a sufficient amount of it must therefore be present so as to exercise this inhibiting effect. The reaction inhibitors to be used can be competitive or non-competitive. Among the competitive inhibitors, several amino acids have been proven the most effective, lysine, arginine and tryptophan being the most prominent ones, and among those, lysine. Among the non-competitive ones, betaine and aminoguanidine derivatives have been proven the most efficient. Choosing the non-competitive inhibitor depends on the non-reducing carbohydrate used, such that in the presence of raffinose, the most effective non-competitive inhibitor is betaine, whereas in the presence of other carbohydrates, the most effective are aminoguanidine derivatives. Therefore, in a particular embodiment, the stabilizing mixture contains an inhibitor of the condensation reaction between carbonyl or carboxyl groups and amine or phosphate groups selected from the group formed by lysine, arginine, tryptophan, betaine, aminoguanidine derivatives, and mixtures thereof.

The main objective of the inert polymer capable of generating a mesh structure preventing the mobility of the dried reagents upon drying the aqueous solution in which it is found is to enhance the stability for storing of the dried reaction mixture by generating a mesh that prevents the mobility of the various reagents composing the reaction mixture, such that to a greater or lesser extent, they are immobilized in the cellules formed by the polymer and, consequently, these reagents cannot get close to one another, thus preventing the chemical reaction of its surface reagent groups. On one hand, the polymer must not react with any of the reagents composing the reaction mixture, and on the other hand, it must create a grid which is fine and moldable enough so as to trap individualized macromolecules in its mesh without distorting their tertiary or quaternary structure when dried. In a particular embodiment, said inert polymer is chosen from the group formed by polyvinylpyrrolidone (PVP), polyethyleneglycol (PEG) of various degrees of polymerization, dextran, starch, the compound called FICOLL[[™]]® polymer (a non-ionic polymer synthesized by copolymerization of sucrose with epichlorohydrin, CAS No. 26873-85-8 from GE Healthcare Bio-Sciences AB), glycogen, acacia gum and mixtures thereof. Generally, glycogen and acacia gum are inert polymers proven to be the most effective ones in their protective function. An additional purpose of this inert polymer is to be used as a cryoprotective agent of the macromolecules present in the reaction mixture to be dried by means of lyophilization, by generating an amorphous mesh that prevents the water from crystallizing during the initial freezing process which is characteristic of that drying process. The inert polymer amount to be added to the drying mixture must be enough so as to ensure the generation of a mesh which is dense enough to prevent the mobility of the macromolecules without it later interfering in the enzymatic reaction that is to occur after rehydrating the dried reaction mixture.

The joint actuation of the three components of the stabilizing mixture (protective agent, inhibitor of the condensation reactions and inert polymer) causes the aforementioned reaction mixtures to be completely functional after drying and prolonged storage. Adding one or two of said components, without the presence of the other two or of the remaining component, generates reaction mixtures which are either not active after drying or their activity disappears a few days after drying, as a consequence, exhibiting a very reduced stability during storage. The non-reducing carbohydrates (protective agents), in conjunction or not with the inhibitor of the condensation reactions, can efficiently protect against drying and stabilize during storage the enzymes and the reaction mixtures containing all the reagents which are necessary for carrying it out except the oligonucleotide primers or probes, but not so with the reaction mixtures containing those oligonucleotides. It also occurs with the non-reducing polyalcohol sorbitol, which is separately shown as a good protective agent and stabilizer of the reaction mixture containing all the reagents which are necessary except the oligonucleotides, but which stops exercising this protective effect when oligonucleotides are present in the reaction mixture. The inhibitor of the condensation reactions, used exclusively in drying or in the presence of the inert polymer, is capable of protecting the reaction mixture without oligonucleotides during the drying process, there being a drop in the yield of the reaction when the reaction mixture contains oligonucleotides.

The aqueous solution of the stabilizing mixture can be prepared outside of the container and subsequently be added to it as is or it can be formed directly in the container by means of adding and mixing the different components of the stabilizing mixture in the container itself.

After mixing the aqueous solution of the reaction mixture with the stabilizing mixture in the container, an aqueous solution is formed comprising the reaction mixture comprising at least one enzyme, together with said stabilizing mixture. Then, all or part of the water contained in the aqueous solution resulting from the reaction mixture with the stabilizing mixture is removed, until obtaining a totally or partially dried mixture comprising the enzyme or enzymes together with said stabilizing mixture and it has a moisture content equal to or less than 30%, thus obtaining a stabilized reaction mixture, which is totally or partially dried, comprising at least one enzyme.

The removal of all or part of the water present in the aqueous solution obtained in the container after mixing the reaction mixture with the stabilizing mixture can be carried out by any conventional drying method, including, for example, lyophilization, drying on a fluidized bed, drying at room temperature and atmospheric pressure, drying at room temperature and reduced pressure, dried at a high temperature and atmospheric pressure, dried at a high temperature and reduced pressure. The preferred drying method is drying at a temperature comprised between 15° C. and 60° C., and a reduced pressure lower than atmospheric pressure. Other methods, such as those previously mentioned, can be applied in drying, although their higher cost or less efficiency or greater aggressiveness against the components of the reaction mixture to be dried dissuade from their use.

The dried, stabilized reaction mixtures provided by this invention have a moisture content which is equal to or less than 30%, preferably equal to or less than 20%.

The completely dried reaction mixtures, i.e., with a residual water presence that is equal to or less than 1%, tend to have a stability during storage which is less than those containing a higher percentage of water, there being a significant decrease in the yields of the reaction after rehydrating and adding the reaction substrate in those that are completely dried. On the other hand, in the dried mixtures containing percentages of residual water comprised between 1% and 20%, the macromolecules exhibit a mobility that may cause undesirable chemical or enzymatic reaction in spite of the presence of the inert polymer that prevents their complete mobility, therefore although they exhibit a several weeks' stability at room temperature (25° C.), they should preferably be stored at temperatures comprised between 4° C. and 10° C. so as to ensure their proper, long term functioning. The selected degree of drying mainly depends on economic factors (the cost of the process, the time necessary for reaching a determined degree of dryness, etc.) and on the existing ratio between the degree of dryness and the stability of the reaction mixture. As a result, in a particular embodiment, the percentage of relative moisture remaining in the stabilized and dried reaction mixture is comprised between 1% and 20%.

By means of the process of the invention, stabilized reaction mixtures, which are totally or partially dried, are obtained, which, in a single tube or well of a plate, contain all the elements which are necessary (for example enzymes, cofactors, substrates, oligonucleotide reaction primers and other additives enhancing or modulating the enzymatic reaction) so that the desired enzymatic reaction can be carried out after rehydrating it and adding the substrate or problem sample, thus avoiding the need to preserve the cold chain in transporting and handling these dried reaction mixtures, simplifying the normal handling which is necessary for carrying out the enzymatic reaction, for example, nucleic acid amplification, by not needing to conserve and add each component of the reaction separately, preventing cross-contaminations and pipetting errors, as a consequence increasing the repeatability and reliability of the analyses. The stabilized reaction mixtures, which are totally or partially dried, maintain their activity with no significant losses thereof, after being transported and conserved at room temperature.

The invention also provides a stabilized and totally or partially dried reaction mixture, with a moisture content which is equal to or less than 30%, preferably comprised between 1% and 20%, comprising at least one enzyme and a stabilizing mixture such as that previously defined comprising (i) at least one protective agent against drying, (ii) at least one inhibitor of the condensation reaction between carbonyl or carboxyl groups and amine or phosphate groups, and (iii) at least one inert polymer capable of generating a mesh structure preventing the mobility of the dried reagents.

In a particular embodiment, said stabilized and totally or partially dried reaction mixture contains an enzyme selected from the group formed by nucleic acid amplification enzymes, restriction enzymes, enzymes intervening in nucleic acid amplification, sequencing or characterization reactions, and mixtures thereof, together with all or part of the reagents which are necessary for carrying out the enzymatic reactions in which said enzymes intervene, preferably with all of said reagents, including cofactors, enzyme substrates and other additives enhancing the enzymatic reactions, it also being possible to optionally include labeled or unlabeled oligonucleotide primers and probes for carrying out a specific amplification, for example, detecting a determined pathogen or genetic mutation in a sample. In this manner, stabilized reaction mixtures, which are totally or partially dried, are obtained, which, in a single tube or well of a plate, contain all the elements which are necessary (i.e., enzymes, cofactors, substrates, oligonucleotide reaction primers and other additives enhancing or modulating the enzymatic reaction) so that the desired reaction can be carried out after rehydrating it and adding the substrate or problem sample.

In a particular embodiment, the invention provides a stabilized reaction mixture, which is totally or partially dried, useful for the amplification of one or more specific sequences of one or several nucleic acids, RNA or DNA, that are present in a sample. Said reaction mixture comprises a DNA polymerase enzyme or a reverse transcriptase enzyme which may or may not be thermostable, deoxynucleotide triphosphates, labeled or unlabeled by any of the known methods, all the necessary cofactors for enzymatic activity and any other additive enhancing or modulating said enzymatic activity. The stabilized and dried reaction mixture can also contain oligonucleotide reaction primers, labeled or unlabeled by means of any of the known methods, which are necessary for the specific amplification of the target nucleotide sequence, and/or the oligonucleotide probes, labeled or unlabeled by any of the known methods, which are necessary for carrying out a hybridization assay, as well as any additive or coadjuvant of the hybridization reaction. This stabilized and dried reaction mixture is in a single container, such as a reaction tube or well of a multi-well plate, and for carrying out the desired reaction, it is only necessary to rehydrate the reaction mixture by means of adding distilled water and the sample to be analyzed. The drying method is preferably that which has been previously explained and contains the described stabilizing mixture.

In another particular embodiment, the invention provides a stabilized and totally or partially dried reaction mixture which is useful for sequencing nucleic acids, wherein dideoxyribonucleotides (ddNTPs) are added to the previously described stabilized and dried reaction mixture, the water soluble dye being eliminated. The drying method is preferably that which has been previously explained and contains the described stabilizing mixture.

In another particular embodiment, the invention provides a stabilized and totally or partially dried reaction mixture which is useful for carrying out restriction analysis on a multi-well plate, such that the sample to be analyzed is deposited on the well containing dried elements of a reaction mixture containing a determined restriction enzyme with which the sample is to be treated, as well as all the cofactors and additives which are necessary for carrying out the restriction analysis, subsequently incubating the sample together with the rehydrated reaction mixture. The drying method is preferably that which has been previously explained and contains the described stabilizing mixture.

In another particular embodiment, the invention provides a stabilized and totally or partially dried reaction mixture useful for sequencing nucleic acids, wherein dideoxyribonucleotides (ddNTPs) are also added to the previously described stabilized and dried mixture, eliminating the water soluble dye. The drying method is preferably that which has been previously explained and contains the described stabilizing mixture.

In another particular embodiment, the invention provides a stabilized and totally or partially dried reaction mixture useful for carrying out restriction analysis on a multi-well plate, such that the sample to be analyzed is deposited on the well containing dried elements of a reaction mixture containing a determined restriction enzyme with which the sample is desired to be treated, as well as all the cofactors and additives which are necessary for carrying out the restriction analysis, subsequently incubating the sample together with the rehydrated reaction mixture. The drying method is preferably that which has been previously explained and contains the described stabilizing mixture.

In another particular embodiment, the invention provides a stabilized and totally or partially dried reaction mixture for carrying out hybridizations on a multi-well plate, such that the sample to be hybridized is deposited on the container containing the dried oligonucleotide probes, which are labeled or unlabeled by any of the known methods, which are necessary for carrying out the hybridization assay, as well as any additive or coadjuvant of the hybridization reaction, subsequently carrying out the hybridization reaction. The drying method is preferably that which has been previously explained and contains the described stabilizing mixture.

The stabilized reaction mixtures, which are totally or partially dried, provided by this invention are of the "ready-to-use" type and have numerous applications, among which are diagnosing diseases, determining DNA sequence, or nucleic acid restriction analysis, in accordance with the methods indicated below and illustrated in the examples accompanying this description.

The stabilized reaction mixtures, which are totally or partially dried, provided by this invention can furthermore be used as a hot-start reaction system. Various studies carried out by the inventors have clearly shown that the amplification reaction with tubes containing said totally or partially dried stabilized reaction mixtures is carried out with the same efficiency whether the content of the tube is re-suspended or not before carrying out the PCR (see Example I). This could mean that the reagents of said totally or partially dried stabilized reaction mixture are effectively released during the first phases of the reaction, for example during incubation at a high temperature. This fact would make said totally or partially dried stabilized reaction mixtures, provided by this invention, perform like a hot-start system. This aspect is highly important for several reasons since:

a) from a practical point of view, it facilitates handling the system by preventing the re-suspension of the mixture [in fact, for large sample volumes (20 tubes or more), the individual re-suspension of each one of them involves a lot of work, up to the point where it could be longer than making a conventional mixture]; whereas on the contrary, not having to perform the re-suspension drastically reduces the work to be performed; and b) from a scientific point of view, the hot-start systems are ideal in amplification systems since they increase the system's specificity; in this sense, the system provided by this invention would permit working comfortably with the tubes on ice and ensure that the reagents are heat released.

The invention also provides a kit comprising a stabilized and totally or partially dried reaction mixture with a moisture content which is equal to or less than 30%, preferably comprised between 1% and 20%, provided by this invention. In a particular embodiment, said kit is one which is suitable for the amplification of one or more specific sequences of one or several nucleic acids, RNA or DNA, present in a sample, or for carrying out a nucleic acid hybridization assay, or for sequencing nucleic acids, or for carrying out the restriction analysis on a multi-well plate, or for carrying out the hybridizations on a multi-well plate. Apart from the totally or partially dried stabilized reaction mixture, comprising at least one enzyme involved in an enzymatic reaction, the kit of the invention contains all or part, preferably all, of the reagents, factors, additives and/or oligonucleotide sequences which are necessary for carrying out the enzymatic reaction.

The following examples explain the present invention in greater detail, and should not be interpreted as a limit to the scope of the invention.

EXAMPLE I

Drying the Reaction Mixture for DNA Amplification

The thermostable DNA polymerase enzyme used in this and in the following examples, unless otherwise indicated, is a *Thermus thermophilus* recombinant DNA polymerase expressed in *Escherichia coli*, property of Biotools B&M Labs, S.A., Spain, and purified by means of a non-chromatographic method developed by the same company (BIOTOOLS™ DNA Polymerase). After its purification, the enzyme was stored at −20° C. in a storage buffer containing 30 mM Tris HCl, pH 8, 25 mM glucose, 25 mM KCl, 0.5 mM PMSF, 0.25% TWEEN™ 20 surfactant and 0.25% NP40™ surfactant. A reaction buffer was prepared containing 750 mM Tris HCl, pH 8, 200 mM $(NH_4)_2SO_4$, 0.1% TWEEN™ 20 surfactant and 20 mM $MgCl_2$.

One microliter of said DNA polymerase enzyme (1 U/µl) conserved in its storage buffer, microliters of the reaction buffer, and 1 microliter of a solution containing the four deoxyribonucleotides (dNTPs) intervening in the DNA amplification reaction (dATP, dCTP, dGTP and dTTP) in an equimolar ratio were added to each 0.2 ml reaction tube used in the experiment. Several tubes were prepared according to the previously described manner, and the suitable volumes of each one of the stabilizing mixtures encompassed in Table 1 were added to each one of them. The tubes thus prepared were dried in an Eppendorf 5301 centrifugal evaporator at temperatures comprised between 10° C. and 60° C. for a time period comprised between 30 and 120 minutes. The previously mentioned temperatures and time periods vary according to the final volume of the mixture to be dried.

After drying, the tubes were conserved at the temperatures and times indicated in Table 1. When the times indicated in Table 1 concluded, their activity was assayed by means of the amplification reaction of a specific region of the cytochrome b, having a size of 359 base pairs (bp), adding 43 microliters of bi-distilled water, 1 microliter of each one of the reaction primers I-1: 5'-CCATCCATCT CAGCATGATG AAA-3' (SEQ ID NO:1); and I-2: 5'-GCCCCTCAGA ATGATATTTG TCCTCA-3' (SEQ ID NO:2), and 500 ng of DNA up to a final volume of 50 microliters.

The gelled content of the vial was re-suspended in half of the tubes by means of pipetting (5 times) in the 50 microliters of added water, primers and DNA. The gelled content from the vial was not re-suspended in the other half of the tubes. An incubation was carried out at 94° C. for 2 minutes (although this incubation cycle is not strictly necessary, but rather optional), and then, 35 cycles of denaturation (94° C., 10 seconds), annealing (55° C., 30 seconds) and extension (72° C., 40 seconds) were performed, using an Eppendorf MASTERCYCLER™ thermal cycler. Similarly, and in order to check the evolution of the activity in the dried tubes, DNA samples were amplified in the same amplification conditions using a fresh mixture.

In every case, the result of the amplification reaction was analyzed in 2% agarose gel (weight/volume), and in all those cases in which the amplification was positive, a single, 359 bp band was found. The activity of the dried reaction mixtures and the fresh mixtures was measured by means of densitometry of the band resulting from the amplification, using a TDI GELPRINTER™ image analyzer to do so, using the GELSUPER™ computer program also developed by TDI. The results of the activity of each dried tube were semi-quantitatively expressed in relation to the results obtained with the fresh mixtures. It was considered that the dried mixtures had:

maximum activity (+++ in Table 1) when the intensity of the band was 90%+10% with regard to the fresh mixture;

optimum activity (++ in Table 1) when the activity ranged between 90% and 50%, low activity (+ in Table 1) when it was less than 50%, and absence of activity (− in Table 1) when the result of the amplification reaction was negative.

The obtained activity results can be seen in the column "example I activity" in Table 1. In conclusion, although several stabilizing mixtures can be considered suitable by having conserved a good activity after drying and subsequently storing the reaction mixture, those which conserve a higher activity are those containing melezitose or palatinitol, in conjunction with lysine and glycogen or acacia gum, or either raffinose with betaine and glycogen.

In all the cases, it was seen that the activity obtained in the tubes in which the gel content of the vial was re-suspended before carrying out the PCR and the activity obtained in the non-re-suspended tubes were similar. This fact seems to demonstrate that there is an effective release of the reagents contained in the gelled mixture during incubation at a high temperature, it would therefore be acting as a hot-start system.

EXAMPLE II

Drying the Reaction Mixture for Reverse RNA Transcription and Subsequent cDNA Amplification The thermostable reverse transcriptase enzyme used in this example was a *Thermus thermophilus* recombinant DNA polymerase with an enhanced reverse transcriptase activity with regard to the enzyme indicated in Example I, expressed in *Escherichia coli*, property of Biotools B&M Labs, S.A. (Spain), and purified by means of a non-chromatographic method developed by the same company (RETROTOOLS™ cDNA/DNA Polymerase). After purifying, the enzyme was stored at −20° C. in a storage buffer containing 30 mM Tris HCl, pH 8, 25 mM glucose, 0.5 mM PMSF, 0.25% TWEEN™ 20 surfactant and 0.25% NP40™ surfactant. A reaction buffer was prepared in order to carry out the reverse transcription which contained 75 mM Tris HCl, pH 8, 200 mM $(NH_4)_2SO_4$, 0.1% TWEEN™ 20 surfactant, 1.5 mM $MnCl_2$ and 0.125 mM of each dNTP (dATP, dGTP, dTTP, dCTP).

1.5 microliters of said enzyme (5 U/µl) conserved in a storage buffer, 4 microliters of the reaction buffer for reverse transcription and 1 microliter of a solution containing dATP, dCTP, dTTP and dGTP in an equimolar ratio were added to each 0.2 microliter reaction tube used in this experiment. 6 microliters of the reaction buffer containing 75 mM Tris HCl, pH 8, 20 mM $(NH_4)_2SO_4$, 0.1% TWEEN™ 20 surfactant, 0.75 mM EGTA and 2 mM $MgCl_2$ were added to another 0.2 ml tube. Several tubes were prepared in the previously described manner, and one of the stabilizing mixtures encompassed in Table 1 was added to each one of them. The tubes thus prepared were dried in an Eppendorf 5301 centrifugal evaporator at temperatures comprised between 10° C. and 60° C. for a time period comprised between 30 and 120 minutes. The previously mentioned temperatures and times vary according to the stabilizing mixture used. After drying, the tubes were conserved at the temperatures and times indicated in Table 1.

The activity of the reaction mixtures, and that of the fresh, non-dried mixtures, was assayed by means of the amplification reaction of a specific region of the CD8α mouse gene, with a size of 1,122 bp, rehydrating the dried mixture with 15 microliters of bi-distilled water, adding 1.25 microliters of the reaction primers:

II-1: 5'-CAAGGATGCT CTTGGCTCTT-3' (SEQ ID NO:3); and

II-2: 5'-GTGGTAGCAG ATGAGAGTGA-3' (SEQ ID NO:4), and 100 ng of messenger RNA extracted from the mouse up to a final volume of 20 microliters. The reverse transcription mixture reconstituted in that manner was incubated at 60° C. for 30 minutes for synthesizing cDNA. Then, the tubes dried with the DNA amplification mixture were rehydrated with 30 µl $H_2O$. The complete volume of the rehydrated reaction buffer was added to the tubes in which the reverse transcription reaction had been carried out. Then, 40 cycles of denaturation (94° C., 45 seconds), annealing (55° C., 30 seconds) and extension (72° C., 1 minute) were carried out, using an Eppendorf MASTERCYCLER™ thermal cycler. The experiment was designed such that the tubes used for the reverse transcription reaction and the tubes used in the subsequent DNA amplification reaction were dried and stored in the same conditions. The amplification products were analyzed by means of electrophoresis in 1% agarose gel (weight/volume), finding a single 1,222 bp band in all those cases in which the amplification was positive. The intensity of the amplification bands of all the samples was measured by means of densitometry of the band resulting from the amplification, using for this a TDI GELPRINTER™ image analyzer, using the GELSUPER™ computer program also developed by TDI. The activity results of each dried tube are semi-quantitatively expressed in relation to the results obtained with the fresh mixtures. It was considered that the dried mixtures had:

maximum activity (+++ in Table 1) when the intensity of the band was 90%+10% with regard to the fresh mixture, optimum activity (++ in Table 1) when the activity ranged between 90% and 50%, low activity (+ in Table 1) when it was less than 50%, and absence of activity (− in Table 1) when the result of the amplification reaction was negative.

The obtained activity results can be seen in the column "example II activity" in Table 1. In conclusion, although several stabilizing mixtures can be considered suitable by having conserved a good activity after drying and subsequently storing the reaction mixture, those which conserve a higher activity are again those containing melezitose or palatinitol, in conjunction with lysine and glycogen or acacia gum, or either raffinose with betaine and glycogen.

EXAMPLE III

Drying Restriction Enzymes in Conjunction with Their Cutting Buffer 1 microliter of the restriction enzyme HindIII (1 U/µl), marketed by MBI Fermentas, Lithuania, was placed in the 1.5 ml Eppendorf tubes used in this experiment together with 1 microliter of the 10× cutting buffer supplied by the manufacturer together with the enzyme. Several tubes were prepared according to the previously described manner, and the suitable volume of each one of the different stabilizing mixtures encompassed in Table 1 was added to them. The tubes thus prepared were dried in an Eppendorf 5301 centrifugal evaporator at temperatures comprised between 10° C. and 60° C. for a time period comprised between 30 and 120 minutes. The previously mentioned temperatures and times vary according to the stabilizing mixture used.

After drying, the tubes were conserved at the temperatures indicated in Table 1. After rehydrating with 8 microliters of bi-distilled water, their activity was assayed once the corresponding time period indicated in said Table 1 had elapsed by means of digesting 0.3 micrograms of lambda phage DNA (150 ng/µl) at 37° C. for 2 hours. An electrophoresis of the result of the digestion reaction was carried out in 1% agarose gel (weight/volume), in parallel with a digestion with a fresh enzyme preparation performed in the same time and temperature conditions. The activity of the dried enzymes was divided into three categories:

A) optimum activity ("digestion" in Table 1) when the complete DNA digestion was obtained, with a restriction pattern that was identical to that obtained upon digesting with the fresh enzyme;

B) average activity ("partial" in Table 1) when a restriction pattern was obtained that was different from that obtained with the fresh enzyme, due to the existence of partial digestions; and C) inactive ("no cut" in Table 1) when the complete absence of digestion was observed.

The results of the comparison of the activity of the dried restriction enzyme together with its cutting buffer regarding the activity exhibited by a digestion of identical features produced by a fresh, non-dried enzyme can be seen in the column "example III activity" in Table 1. In conclusion, again, those stabilizing mixtures containing melezitose or palatinitol, in conjunction with lysine and glycogen or acacia gum, or either raffinose with betaine and glycogen are those which generate complete digestions in longer conservation times, whereas the other assayed mixtures generate partial digestions or they do not cut.

Other restriction enzymes such as Mbo I, Bgl II, Rsa I, Ava I, Ava II and Acc I were likewise assayed with identical results.

EXAMPLE IV

Drying a reaction mixture including oligonucleotide primers in a tube and on a multi-well plate for the specific amplification of a determined DNA sequence A reaction mixture was prepared containing, in addition to all the components specified in Example I, the reaction primers described in Spanish patent application number P200100568 and which serve so as to identify the 4 *Plasmodium* species which cause the development of malaria in humans, as well as human DNA, which serves as a positive reaction control in a single, multiplexed amplification reaction by means of a semi-nested reaction mechanism in a single step. In this method, human DNA samples are analyzed which have been extracted from whole blood by means of conventional methods.

The simultaneous DNA amplification reaction of each one of the 4 *Plasmodium* species and of the human DNA amplification control is carried out by including 25 µl of a reaction mixture with the following composition in a separate reaction tube (of 0.2 ml or 0.5 ml): 75 mM TRIZMA™ base, 20 mM ammonium sulfate, 0.1% TWEEN™ 20 surfactant, 5 mM $MgCl_2$, 0.5 mM dATP, 0.5 mM dCTP, 0.5 mM dGTP, 0.5 mM dTTP, 0.04 µM H1 primer (SEQ ID NO: 5), 0.04 µM H2 primer (SEQ ID NO: 6), 2.25 µM P1 primer (SEQ ID NO: 7), 0.01 µM P2 primer (SEQ ID NO: 8), 0.6 µM F primer (SEQ ID NO: 9), 0.15 µM M primer (SEQ ID NO: 10), 0.375 µM 0 primer (SEQ ID NO: 11), 0.15 µM V primer (SEQ ID NO: 12) and 2 units of DNA polymerase (BIOTOOLS™ DNA polymerase).

Several tubes were prepared according to the previously described manner, and one of the stabilizing mixtures encompassed in Table 1 was added to each one of them, at different concentrations of each one of the elements integrating the mixtures. The tubes thus prepared were dried in an Eppendorf 5301 centrifugal evaporator at temperatures comprised between 10° C. and 60° C. for a time period comprised between 30 and 120 minutes. The previously mentioned temperatures and times vary according to the stabilizing mixture used.

After drying, the tubes were conserved at the temperatures indicated in Table 1. After the conservation periods indicated in said Table 1, their activity was assayed after rehydrating the dried mixture with 20 microliters of bi-distilled water and 50 ng of DNA proceeding from patients infected with different *Plasmodium* species, up to a final volume of 25 microliters. Likewise, and as a reference of the activity, tubes with fresh, non-dried mixture were included in all the experiments. The amplification cycles used include an initial heating cycle at 85° C. for 3 minutes, followed by a denaturation step at 94° C. for 7 minutes. Then, the amplification round is carried out, consisting of 40 repeated cycles, each one of which has a denaturation step at 94° C. for 45 seconds, a hybridization step at 62° C. for 45 seconds and an elongation step at 72° C. for 1 minute. Once the 40 amplification cycles have finished, a final elongation step is carried out at 72° C. for 10 minutes. The amplification reaction was carried out in an Eppendorf MASTERCYCLER™ thermal cycler. An electrophoresis of the amplification result was performed in 2% agarose gel (weight/volume), and in all those cases in which the amplification was positive, 2 bands of 395 bp and 231 bp were found, corresponding to the amplification products of the *P. falciparum* and human DNA, respectively. The activity of the dried reaction mixture was measured by means of densitometry of the band resulting from the amplification, using for this a TDI GELPRINTER™ image analyzer, using the GELSUPER™ computer program also developed by TDI. The activity results of each dried tube are semi-quantitatively expressed in relation to the results obtained with the fresh mixtures. It was considered that the dried mixtures had:

maximum activity (+++ in Table 1) when the intensity of the band was 90%+10% with regard to the fresh mixture, optimum activity (++ in Table 1) when the activity ranged between 90% and 50%, low activity (+ in Table 1) when it was less than 50%, and absence of activity (− in Table 1) when the result of the amplification reaction was negative.

The obtained activity results can be seen in the column "example IV activity" in Table 1. In conclusion, although several stabilizing mixtures can be considered suitable by having conserved a good activity after drying and subsequently storing the reaction mixture, those which conserve a higher activity are those containing melezitose or palatinitol, in conjunction with lysine and glycogen or acacia gum, or either raffinose with betaine and glycogen.

An identical analytical process was followed by depositing the previously mentioned reaction mixture containing the oligonucleotide primers on each well of a NUNC™ polystyrene multi-well plate, drying the plate by means of introducing it in a dryer and creating a vacuum by means of a pump. A plate was prepared for each temperature and time point, subsequently analyzed. Likewise, fresh, non-dried wells were prepared in each experiment as an activity reference. The amplification conditions and results analysis were identical to those previously described. The dried sample activity measurement results fully coincide with those obtained for the case of the previously mentioned tubes.

EXAMPLE V

Drying a Reaction Mixture Including Oligonucleotide Primers in a Tube and on a Multi-well Plate for the Specific Amplification of a Determined RNA Sequence A reaction mixture was prepared containing, in addition to all the components specified in Example II, the reaction primers described in Spanish patent application number P200100567 and which serve to generically detect the enterovirus genome by means of a coupled reverse transcription system followed by a semi-nested amplification reaction in a single tube or well.

In order to carry out the reverse transcription reaction, for each reaction 20 microliters of a mixture are prepared containing 75 mM Tris HCl, 20 mM $(NH_4)_2SO_4$, 0.1% TWEEN™ 20 surfactant, 1.5 mM $MnCl_2$, 0.125 mM of each dNTP (dATP, dCTP, dGTP and dTTP) and 10 picomoles of EV1M primer: 5'-ACCCAAAGTA GTCGGTTCCG C-3' (SEQ ID NO: 13) and 7.5 units of the DNA polymerase enzyme indicated in Example II.

In order to carry out the DNA amplification reaction, 30 microliters of a mixture are prepared for each reaction which contain 75 mM Tris HCl, pH 8, 20 mM $(NH_4)_2SO_4$, 0.01% TWEEN™ 20 surfactant, 0.75 mM EGTA, 2 mM $MgCl_2$, 10 picomoles of EV2P primer: 5'-CAAGCATTCT GTTTC-CCC-3' (SEQ ID NO: 14) and 0.5 picomoles of EVIP primer: 5'-CGGTACCTTT GTRCGCCTGT T-3' (SEQ ID NO: 15).

Several tubes were prepared in the previously described manner and different volumes of each one of the stabilizing mixtures appearing in Table 1 were added to each one of them. The tubes thus prepared were dried in an Eppendorf 5301 centrifugal evaporator at temperatures comprised between 10° C. and 60° C. for a time period comprised between 30 and 120 minutes. The previously mentioned temperatures and times vary according to the stabilizing mixture used.

After drying, the tubes were conserved at the temperatures and times indicated in Table 1. Their activity was assayed in the times also indicated in Table 1, after rehydrating the dried reverse transcription mixture with 15 microliters of bi-distilled water, adding 100 ng of RNA up to a final volume of 20 microliters. Four cycles of 48° C./5 minutes and 60° C./15 minutes were performed. The 0.2 ml tube used in the subsequent DNA amplification reaction, which contains the same stabilizing mixture as its homologue used for the reverse transcription, was re-suspended in 30 microliters of bi-distilled water, and its volume was added on the 0.2 ml tube containing the reverse transcription product. 35 cycles of denaturation (94° C., 1 minute), annealing (48° C., 1 minute) and extension (72° C., 1 minute) were carried out, using an Eppendorf MASTERCYCLER™ thermal cycler. An electrophoresis of the amplification reaction result was carried out in 2% agarose gel (weight/volume), and in all cases, it was found that the amplification was positive, showing 2 bands of 390 bp and 489 bp. In all the experiments, tubes with a fresh mixtures were included that were used as an activity reference. The activity of the dried and fresh reaction mixtures was measured by means of densitometry of the band resulting from the amplification, using for this a TDI GELPRINTER™ image analyzer, using the GELSUPER™ computer program also developed by TDI. It was considered that the dried mixtures had:

maximum activity (+++ in Table 1) when the intensity of the band was 90%+10% with regard to the fresh mixture, optimum activity (++ in Table 1) when the activity ranged between 90% and 50%, low activity (+ in Table 1) when it was less than 50%, and absence of activity (− in Table 1) when the result of the amplification reaction was negative.

The obtained activity results can be seen in the column "example V activity" in Table 1. In conclusion, although several stabilizing mixtures can be considered suitable by having conserved a good activity after drying and subsequently storing the reaction mixture, those which conserve a higher activity are those containing melezitose or palatinitol, in conjunction with lysine and glycogen or acacia gum, or raffinose with betaine and glycogen.

An identical analytical process was followed by depositing said reaction mixture containing the oligonucleotide primers on each well of a NUNC™ polystyrene multi-well plate, drying the plate by means of introducing it in a dryer and creating a vacuum by means of a pump. A plate was prepared for each temperature and time point, subsequently analyzed. Likewise, fresh, non-dried wells were prepared in each experiment as an activity reference. The amplification conditions and results analysis were identical to those previously described. The dried sample activity measurement results fully coincide with those obtained for the case of the previously mentioned tubes.

EXAMPLE VI

Drying a Reaction Mixture Including Oligonucleotide Primers in a Tube and on a Multi-well Plate for the Specific Amplification of a Determined DNA Sequence Which is Subsequently Subjected to Restriction Analysis on a Multi-well Plate, Each One of the Wells Containing Dried Restriction Enzymes Which are Necessary for Carrying Out Said Analysis This system was assayed by using a papillomavirus identification and classifying method. Said method consists of a first co-amplification step of two regions of the viral genome: a 450 by fragment of region L1 conserved in the genome of all the papillomaviruses, and a 250 by fragment of the E6-E7 region which is only present in oncogenic papillomaviruses. The amplification mixture contains 75 mM TRIZMA™ base, 20 mM ammonium sulfate, 0.01% TWEEN™ 20 surfactant, 2 mM $MgCl_2$, 0.2 mM dATP, 0.2 mM dCTP, 0.2 mM dGTP, 0.2 mM dTTP, 2.5 picomoles of the primers:

VI-1: 5'-GCMCAGGGWC ATAAYAATGG-3' (SEQ ID NO: 16), and

VI-2: 5'-CGTCCMARRG GAWACTGATC-3' (SEQ ID NO: 17), 1.25 picomoles of the primers:

VI-3: 5'-TGTCAAAAAC CGTTGTGTCC-3' (SEQ ID NO: 18), and

VI-4: 5'-GAGCTGTCGC TTAATTGCTC-3' (SEQ ID NO: 19), and 1 unit of the DNA polymerase enzyme indicated in Example I. The analysis of the products of this amplification permits identifying the presence of the papillomavirus (450 by band) as well as determining if there is any oncogenic species (250 by band). Then, the digestion with 5 restriction enzymes (Rsa I, Acc I, Ava I, Ava II and Bgl II) permits characterizing the papilloma species present in each sample. Thus, the amplified 250 by band (corresponding to an oncogenic genome) of HPV 16, HPV 18 and HPV 33 is digested only by Ava II, yielding in each case a different restriction standard that is easily differentiable in agarose gels, that of HPV 31 is digested by Rsa I, that of HPV 35 by Ava I, that of HPV 52b by Bgl II and that of HPV 58 by Acc I. It is also possible to classify the non-oncogenic genotypes by the digestion standard of the 450 by band with the Rsa I activity.

Several tubes were prepared in the previously described manner and different volumes of the stabilizing mixtures indicated in Table 1 were added to each one of them. Tubes were also prepared with each one of the previously mentioned restriction enzymes (1 unit of each enzyme per tube) and 1 microliter of the respective 10 X reaction buffers. All the tubes thus prepared were dried in an Eppendorf 5301 centrifugal evaporator at temperatures comprised between 10° C. and 60° C. for a time period comprised between 30 and 120 minutes. The previously mentioned temperatures and times vary according to the stabilizing mixture used.

After drying, the tubes were conserved at the temperatures and times indicated in Table 1. Once the conservation periods as indicated in Table 1 had elapsed, their activity was assayed after rehydrating the dried mixture with 45 microliters of bi-distilled water and 25 ng of DNA extracted from a patient infected with HPV 18, up to a final volume of 50 microliters. Thirty cycles of denaturation (94° C., 30 seconds), annealing (50° C., 1 minute) and extension (72° C., 1 minute) were carried out, using an Eppendorf MASTERCYCLER™ thermal cycler. An electrophoresis of the amplification reaction result was carried out in 2% agarose gel (weight/volume), and in all those cases in which the amplification was positive, 2 bands of 250 bp and 450 bp, respectively, were found. The dried reaction mixture activity was measured by means of densitometry of the band resulting from the amplification, using for this a TDI GELPRINTER™ image analyzer, using the GELSUPER™ computer program also developed by TDI. It was considered that the dried mixtures had:

maximum activity (+++ in Table 1) when the intensity of the band was 90%+10% with regard to the fresh mixture, optimum activity (++ in Table 1) when the activity ranged between 90% and 50%, low activity (+ in Table 1) when it was less than 50%, and absence of activity (− in Table 1) when the result of the amplification reaction was negative.

Then, the tubes and wells dried with the restriction enzymes were re-suspended with 10 microliters of the amplifications carried out with the fresh mixture. After incubating the mixtures at 37° C. for 30 minutes, the digestion products were analyzed in 1.5% agarose. It is considered:

optimum activity ("digestion" in Table 1) is the complete digestion of the 250 base pair (bp) bands, average activity ("partial" in Table 1) is the partial digestion of the bands, and inactive ("no cut" in Table 1) is the complete absence of digestion.

The densitometry results obtained after carrying out the amplification reactions can be seen in the column "example VI activity" in Table 1. In conclusion, although several stabilizing mixtures can be considered suitable by having conserved a good activity after drying and subsequently storing the reaction mixture, those which conserve a higher activity are those containing melezitose or palatinitol, in conjunction with lysine and glycogen or acacia gum, or raffinose with betaine and glycogen.

With regard to the activity of the restriction enzymes, optimum results were obtained with the five enzymes used in those cases in which the mixture used in drying the restriction enzyme contains melezitose or palatinitol, in conjunction with lysine and glycogen or acacia gum, or raffinose with betaine and glycogen.

An identical analytical process was followed by depositing said reaction mixture containing the oligonucleotide primers on each well of a NUNC™ polystyrene multi-well plate, drying the plate by means of introducing it in a dryer and creating a vacuum by means of a pump. A plate was prepared for each temperature and time point, subsequently analyzed. Likewise, fresh, non-dried wells were prepared in each experiment as an activity reference. The amplification conditions and results analysis were identical to those previously described. The dried sample activity measurement results fully coincide with those obtained for the case of the previously mentioned tubes.

EXAMPLE VII

Amplifying a Determined DNA Sequence on a Multi-well Plate with Covalently Bound Oligonucleotides and a Dried Reaction Mixture, Which is Subsequently Analyzed by Means of Hybridization With a Biotinylated Probe This system was used to amplify and identify clinical samples of *Plasmodium* DNA. To do so, polystyrene multi-well plates (COVALINK™ NH MICROWELLS™, NUNC™) were used. The generic *Plasmodium* P1 primer, indicated in Example IV, had previously been covalently bound to each one of the wells of the plate through its 5' end, and which will serve as a primer in the subsequent amplification reaction. The reaction mixture described in Example IV was added to each well of the plates, as well as the different stabilizing mixtures as they are described in Example IV and in Table 1. As many plates were prepared as storage time and temperature points that were going to be subsequently assayed (Table 1). Once the plates were prepared, they were dried by means of introducing them in a dryer and creating a vacuum by means of a pump.

The dried samples were rehydrated with 20 microliters of sterile water, and 5 microliters of DNA from patients infected with *Plasmodium* were added at a concentration of 10 ng/μl. Then, the amplification reaction was carried out in the conditions described in Example IV, using an Eppendorf GRADIENT™ thermal cycler for multi-well plates. In every case, an amplification was carried out in the same conditions using a non-dried plate in order to be used as an activity reference.

Once the reaction was finished, the reaction mixture was removed from each well, such that in the well only the double-band amplification product remained bound in the well. Given that one of the bands was synthesized by elongation as from the generic P1 primer, this band remained covalently bonded to the well. On the contrary, the other DNA band is bonded to the first one by means of complementary base pairing. Given that it is necessary to use a single DNA band as a substrate for the subsequent hybridization reaction, the plates were washed with the object of eliminating the DNA band that is not covalently bound to the well, and only leave the band synthesized as from the P1 oligonucleotide. To do so, a reaction buffer was prepared whose composition was 50% formamide, 5×SSC and 0.1% SDS. Fifty microliters of this mixture were added to each well and incubated for 10 minutes at 80° C. Then, the mixture was removed and the washing process was repeated three times.

The hybridization reactions were carried out by using a biotinylated oligonucleotide. For this, each well was incubated with 100 femtomoles of the probe in the hybridization reaction buffer containing 4×SSC, 10×Denhart and 200 µg/ml of salmon sperm DNA for two hours at 60° C. Then, the hybridization mixture was removed and each well was washed twice with 200 µl of a 0.1×SSC dilution, followed by washing in a 100 mM maleic acid reaction buffer, pH 7.5, 150 mM NaCl and 0.3% TWEEN™ 20 surfactant, and a final washing in a 100 mM maleic acid blocking reaction buffer, pH 7.5, 150 mM NaCl and 0.1% BSA. Once the blockings were finished, 1:2000 streptavidin conjugated with peroxidase in the previously described blocking reaction buffer was added to each well, and was incubated at 23° C. for 45 minutes. Lastly, the wells were washed three times with 200 microliters of 100 mM maleic acid reaction buffer, pH 7.5, 150 mM NaCl and 0.3% TWEEN™ 20 surfactant and once with 200 microliters of 100 mM maleic acid reaction buffer, pH 7.5 and 150 mM NaCl. Finally, 100 microliters of TMB were added to each well, and it was incubated for 10 minutes in the dark. After stopping the reaction, the absorbance was determined at 450 nm, all the values being corrected with the absorbance value of plastic at 655 nm.

It was considered that the dried mixtures had:
maximum activity (+++ in Table 1) when the absorbance measurement was 90%+10% with regard to the fresh mixture,
optimum activity (++ in Table 1) when it ranged between 90% and 50%,
low activity (+ in Table 1) when it was less than 50%, and
absence of activity (− in Table 1) when the absorbance measurement was similar to that obtained in wells that had not contained any reaction mixture.

The obtained activity results can be seen in the column "example VII activity" in Table 1. In conclusion, although several stabilizing mixtures can be considered suitable by having conserved a good activity after drying and subsequently storing the reaction mixture, those which conserve a higher activity are again those containing melezitose or palatinitol, in conjunction with lysine and glycogen or acacia gum, or raffinose with betaine and glycogen.

| REACTION MIXTURE | conservation temperature | conservation time (days) | example I activity | example II activity | example III activity | example IV activity | example V activity | example VI activity | example VII activity |
|---|---|---|---|---|---|---|---|---|---|
| Sucrose | 37° C. | 1 | + | + | Partial | + | + | + | + |
| | 50° C. | 1 | − | − | No cut | − | − | − | − |
| | 25° C. | 8 | − | − | No cut | − | − | − | − |
| | 37° C. | 8 | − | − | No cut | − | − | − | − |
| | 50° C. | 8 | − | − | No cut | − | − | − | − |
| | 4° C. | 15 | − | − | No cut | − | − | − | − |
| | 25° C. | 15 | − | − | No cut | − | − | − | − |
| | 37° C. | 15 | − | − | No cut | − | − | − | − |
| | 4° C. | 30 | − | − | No cut | − | − | − | − |
| | 25° C. | 30 | − | − | No cut | − | − | − | − |
| | 4° C. | 60 | − | − | No cut | − | − | − | − |
| Raffinose | 37° C. | 1 | + | + | Partial | + | + | + | + |
| | 50° C. | 1 | − | − | No cut | − | − | − | − |
| | 25° C. | 8 | + | + | No cut | + | − | + | + |
| | 37° C. | 8 | − | − | No cut | − | − | − | − |
| | 50° C. | 8 | − | − | No cut | − | − | − | − |
| | 4° C. | 15 | − | − | No cut | − | − | − | − |
| | 25° C. | 15 | − | − | No cut | − | − | − | − |
| | 37° C. | 15 | − | − | No cut | − | − | − | − |
| | 4° C. | 30 | − | − | No cut | − | − | − | − |
| | 25° C. | 30 | − | − | No cut | − | − | − | − |
| | 4° C. | 60 | − | − | No cut | − | − | − | − |
| Palatinitol | 37° C. | 1 | + | + | Cut | + | + | + | + |
| | 50° C. | 1 | + | + | Partial | + | + | + | + |
| | 25° C. | 8 | − | − | No cut | − | − | − | − |
| | 37° C. | 8 | − | − | No cut | − | − | − | − |
| | 50° C. | 8 | − | − | No cut | − | − | − | − |
| | 4° C. | 15 | − | − | Partial | − | − | − | − |
| | 25° C. | 15 | − | − | No cut | − | − | − | − |
| | 37° C. | 15 | − | − | No cut | − | − | − | − |
| | 4° C. | 30 | − | − | No cut | − | − | − | − |
| | 25° C. | 30 | − | − | No cut | − | − | − | − |
| | 4° C. | 60 | − | − | No cut | − | − | − | − |
| Melezitose | 37° C. | 1 | + | + | Cut | ++ | + | + | + |
| | 50° C. | 1 | + | + | Cut | + | + | + | + |
| | 25° C. | 8 | − | − | Partial | − | − | − | − |
| | 37° C. | 8 | − | − | No cut | − | − | − | − |
| | 50° C. | 8 | − | − | No cut | − | − | − | − |
| | 4° C. | 15 | − | − | Partial | − | − | − | − |
| | 25° C. | 15 | − | − | No cut | − | − | − | − |
| | 37° C. | 15 | − | − | No cut | − | − | − | − |
| | 4° C. | 30 | − | − | No cut | − | − | − | − |
| | 25° C. | 30 | − | − | No cut | − | − | − | − |
| | 4° C. | 60 | − | − | No cut | − | − | − | − |
| Glycerol | 37° C. | 1 | ++ | Cut | ++ | ++ | ++ | ++ | |
| | 50° C. | 1 | + | + | Cut | + | + | + | + |
| | 25° C. | 8 | + | + | Partial | + | + | + | + |
| | 7° C. | 8 | + | − | Partial | + | + | + | + |
| | 0° C. | 8 | − | − | No cut | − | − | − | − |
| | 4° C. | 15 | + | + | Partial | + | + | + | + |
| | 25° C. | 15 | − | − | No cut | − | − | − | − |
| | 37° C. | 15 | − | − | No cut | − | − | − | − |

| REACTION MIXTURE | conservation temperature | conservation time (days) | example I activity | example II activity | example III activity | example IV activity | example V activity | example VI activity | example VII activity |
|---|---|---|---|---|---|---|---|---|---|
| | 4° C. | 30 | − | − | No cut | − | − | − | − |
| | 25° C. | 30 | − | − | No cut | − | − | − | − |
| | 4° C. | 60 | − | − | No cut | − | − | − | − |
| Lysine | 37° C. | 1 | ++ | ++ | Cut | ++ | + | ++ | + |
| | 50° C. | 1 | − | − | No cut | − | − | − | − |
| | 25° C. | 8 | − | − | No cut | − | − | − | − |
| | 37° C. | 8 | − | − | No cut | − | − | − | − |
| | 50° C. | 8 | − | − | No cut | − | − | − | − |
| | ° C. | 15 | − | − | No cut | − | − | − | − |
| | 5° C. | 15 | − | − | No cut | − | − | − | − |
| | 7° C. | 15 | − | − | No cut | − | − | − | − |
| | ° C. | 30 | − | − | No cut | − | − | − | − |
| | 5° C. | 30 | − | − | No cut | − | − | − | − |
| | ° C. | 60 | − | − | No cut | − | − | − | − |
| Glycogen | 37° C. | 1 | ++ | ++ | Cut | ++ | ++ | ++ | ++ |
| | 50° C. | 1 | + | + | Partial | + | + | + | + |
| | 25° C. | 8 | + | + | Partial | + | + | + | + |
| | 37° C. | 8 | − | − | No cut | − | − | − | − |
| | 50° C. | 8 | − | − | No cut | − | − | − | − |
| | 4° C. | 15 | − | − | Partial | − | − | − | − |
| | 25° C. | 15 | − | − | No cut | − | − | − | − |
| | 37° C. | 15 | − | − | No cut | − | − | − | − |
| | 4° C. | 30 | − | − | No cut | − | − | − | − |
| | 25° C. | 30 | − | − | No cut | − | − | − | − |
| | 4° C. | 60 | − | − | No cut | − | − | − | − |
| Trehalose + Lysine | 37° C. | 1 | +++ | +++ | Cut | +++ | +++ | +++ | +++ |
| | 50° C. | 1 | ++ | ++ | Cut | ++ | ++ | ++ | ++ |
| | 25° C. | 8 | ++ | ++ | Cut | ++ | ++ | ++ | ++ |
| | 37° C. | 8 | + | + | Partial | + | + | + | + |
| | 50° C. | 8 | − | − | No cut | − | − | − | − |
| | 4° C. | 15 | + | ++ | Partial | + | + | + | + |
| | 25° C. | 15 | − | − | No cut | − | − | − | − |
| | 37° C. | 15 | − | − | No cut | − | − | − | − |
| | 4° C. | 30 | − | − | No cut | − | − | − | − |
| | 25° C. | 30 | − | − | No cut | − | − | − | − |
| | 4° C. | 60 | − | − | No cut | − | − | − | − |
| Trehalose + PVP | 37° C. | 1 | + | + | Cut | + | + | + | + |
| | 50° C. | 1 | − | − | Partial | − | − | − | − |
| | 25° C. | 8 | − | − | No cut | − | − | − | − |
| | 37° C. | 8 | − | − | No cut | − | − | − | − |
| | 50° C. | 8 | − | − | No cut | − | − | − | − |
| | 4° C. | 15 | − | − | No cut | − | − | − | − |
| | 25° C. | 15 | − | − | No cut | − | − | − | − |
| | 37° C. | 15 | − | − | No cut | − | − | − | − |
| | 4° C. | 30 | − | − | No cut | − | − | − | − |
| | 25° C. | 30 | − | − | No cut | − | − | − | − |
| | 4° C. | 60 | − | − | No cut | − | − | − | − |
| Sorbitol + PEG | 37° C. | 1 | ++ | ++ | Cut | + | + | + | + |
| | 50° C. | 1 | + | + | Partial | + | + | + | + |
| | 25° C. | 8 | − | − | No cut | − | − | − | − |
| | 37° C. | 8 | − | − | No cut | − | − | − | − |
| | 50° C. | 8 | − | − | No cut | − | − | − | − |
| | 4° C. | 15 | − | − | No cut | − | − | − | − |
| | 25° C. | 15 | − | − | No cut | − | − | − | − |
| | 37° C. | 15 | − | − | No cut | − | − | − | − |
| | 4° C. | 30 | − | − | No cut | − | − | − | − |
| | 25° C. | 30 | − | − | No cut | − | − | − | − |
| | 4° C. | 60 | − | − | No cut | − | − | − | − |
| Raffinose + betaine | 37° C. | 1 | ++ | ++ | Cut | ++ | ++ | ++ | ++ |
| | 50° C. | 1 | + | + | Partial | + | + | + | + |
| | 25° C. | 8 | + | + | Partial | + | + | + | + |
| | 37° C. | 8 | + | − | No cut | + | − | + | + |
| | 50° C. | 8 | − | − | No cut | − | − | − | − |
| | 4° C. | 15 | + | + | Partial | − | − | − | − |
| | 25° C. | 15 | − | − | No cut | − | − | − | − |
| | 37° C. | 15 | − | − | No cut | − | − | − | − |
| | 4° C. | 30 | − | − | No cut | − | − | − | − |
| | 25° C. | 30 | − | − | No cut | − | − | − | − |
| | 4° C. | 60 | − | − | No cut | − | − | − | − |
| Melezitose + Lysine | 37° C. | 1 | ++ | ++ | Cut | ++ | ++ | ++ | ++ |
| | 50° C. | 1 | + | + | Partial | + | + | + | + |
| | 25° C. | 8 | + | + | Partial | + | + | + | + |
| | 37° C. | 8 | − | − | No cut | − | − | − | − |
| | 50° C. | 8 | − | − | No cut | − | − | − | − |
| | 4° C. | 15 | + | − | Partial | + | − | − | − |
| | 25° C. | 15 | − | − | No cut | − | − | − | − |

-continued

| REACTION MIXTURE | conservation temperature | conservation time (days) | example I activity | example II activity | example III activity | example IV activity | example V activity | example VI activity | example VII activity |
|---|---|---|---|---|---|---|---|---|---|
| | 37° C. | 15 | − | − | No cut | − | − | − | − |
| | 4° C. | 30 | − | − | No cut | − | − | − | − |
| | 25° C. | 30 | − | − | No cut | − | − | − | − |
| | 4° C. | 60 | − | − | No cut | − | − | − | − |
| Melezitose + glycogen | 37° C. | 1 | + | + | Partial | + | + | + | + |
| | 50° C. | 1 | − | − | No cut | − | − | − | − |
| | 25° C. | 8 | − | − | No cut | − | − | − | − |
| | 37° C. | 8 | − | − | No cut | − | − | − | − |
| | 50° C. | 8 | − | − | No cut | − | − | − | − |
| | 4° C. | 15 | − | − | No cut | − | − | − | − |
| | 25° C. | 15 | − | − | No cut | − | − | − | − |
| | 37° C. | 15 | − | − | No cut | − | − | − | − |
| | 4° C. | 30 | − | − | No cut | − | − | − | − |
| | 25° C. | 30 | − | − | No cut | − | − | − | − |
| | 4° C. | 60 | − | − | No cut | − | − | − | − |
| Lysine + glycogen | 37° C. | 1 | ++ | ++ | Cut | ++ | ++ | ++ | ++ |
| | 50° C. | 1 | + | + | Partial | + | + | + | + |
| | 25° C. | 8 | + | + | Partial | + | + | + | + |
| | 37° C. | 8 | − | − | No cut | − | − | − | − |
| | 50° C. | 8 | − | − | No cut | − | − | − | − |
| | 4° C. | 15 | − | − | No cut | − | − | − | − |
| | 25° C. | 15 | − | − | No cut | − | − | − | − |
| | 37° C. | 15 | − | − | No cut | − | − | − | − |
| | 4° C. | 30 | − | − | No cut | − | − | − | − |
| | 25° C. | 30 | − | − | No cut | − | − | − | − |
| | 4° C. | 60 | − | − | No cut | − | − | − | − |
| Melezitose + lysine + PEG | 37° C. | 1 | ++ | ++ | Cut | ++ | ++ | ++ | ++ |
| | 50° C. | 1 | + | + | Partial | + | + | + | + |
| | 25° C. | 8 | + | + | Partial | + | + | + | + |
| | 37° C. | 8 | − | − | Partial | − | − | − | − |
| | 50° C. | 8 | − | − | No cut | − | − | − | − |
| | 4° C. | 15 | + | + | Partial | + | + | − | − |
| | 25° C. | 15 | − | − | No cut | − | − | − | − |
| | 37° C. | 15 | − | − | No cut | − | − | − | − |
| | 4° C. | 30 | − | − | No cut | − | − | − | − |
| | 25° C. | 30 | − | − | No cut | − | − | − | − |
| | 4° C. | 60 | − | − | No cut | − | − | − | − |
| Melezitose + lysine + PVP | 37° C. | 1 | + | + | Cut | + | + | + | + |
| | 50° C. | 1 | − | − | No cut | − | − | − | − |
| | 25° C. | 8 | − | − | No cut | − | − | − | − |
| | 37° C. | 8 | − | − | No cut | − | − | − | − |
| | 50° C. | 8 | − | − | No cut | − | − | − | − |
| | 4° C. | 15 | + | + | Partial | + | + | − | − |
| | 25° C. | 15 | − | − | No cut | − | − | − | − |
| | 7° C. | 15 | − | − | No cut | − | − | − | − |
| | 4° C. | 30 | − | − | No cut | − | − | − | − |
| | 25° C. | 30 | − | − | No cut | − | − | − | − |
| | 4° C. | 60 | − | − | No cut | − | − | − | − |
| Melezitose + lysine + dextran | 37° C. | 1 | − | − | No cut | − | − | − | − |
| | 50° C. | 1 | − | − | No cut | − | − | − | − |
| | 25° C. | 8 | − | − | No cut | − | − | − | − |
| | 37° C. | 8 | − | − | No cut | − | − | − | − |
| | 50° C. | 8 | − | − | No cut | − | − | − | − |
| | 4° C. | 15 | − | − | No cut | − | − | − | − |
| | 25° C. 15 | − | − | No cut | − | − | − | − | |
| | 37° C. | 15 | − | − | No cut | − | − | − | − |
| | 4° C. | 30 | − | − | No cut | − | − | − | − |
| | 25° C. | 30 | − | − | No cut | − | − | − | − |
| | 4° C. | 60 | − | − | No cut | − | − | − | − |
| Melezitose + lysine + glycogen | 37° C. | 1 | +++ | +++ | Cut | ++++ | +++ | +++ | +++ |
| | 50° C. | 1 | ++ | ++ | Cut | ++ | ++ | +++ | +++ |
| | 25° C. | 8 | ++ | ++ | Cut | ++ | ++ | ++ | ++ |
| | 37° C. | 8 | + | + | Partial | + | + | + | + |
| | 50° C. | 8 | − | − | No cut | − | − | − | − |
| | 4° C. | 15 | ++ | ++ | Cut | ++ | ++ | +++ | +++ |
| | 25° C. | 15 | + | + | Partial | + | + | + | + |
| | 37° C. | 15 | − | − | No cut | − | − | − | − |
| | 4° C. | 30 | ++ | ++ | Cut | ++ | ++ | ++ | ++ |
| | 25° C. | 30 | − | − | No cut | − | − | − | − |
| | 4° C. | 60 | ++ | ++ | Cut | ++ | ++ | ++ | ++ |
| Melezitose + lysine + acacia gum | 37° C. | 1 | +++ | +++ | Cut | +++ | +++ | +++ | +++ |
| | 50° C. | 1 | ++ | ++ | Cut | ++ | ++ | ++ | ++ |
| | 25° C. | 8 | ++ | ++ | Cut | ++ | ++ | ++ | ++ |
| | 37° C. | 8 | + | + | Partial | + | + | + | + |
| | 50° C. | 8 | − | − | No cut | − | − | − | − |
| | 4° C. | 15 | ++ | ++ | Cut | ++ | ++ | + | + |

-continued

| REACTION MIXTURE | conservation temperature | conservation time (days) | example I activity | example II activity | example III activity | example IV activity | example V activity | example VI activity | example VII activity |
|---|---|---|---|---|---|---|---|---|---|
| | 25° C. | 15 | − | − | No cut | − | − | − | − |
| | 37° C. | 15 | − | − | No cut | − | − | − | − |
| | 4° C. | 30 | + | + | Partial | + | + | + | + |
| | 25° C. | 30 | − | − | No cut | − | − | − | − |
| | 4° C. | 60 | + | + | Partial | + | + | + | + |
| Melezitose + betaine + glycogen | 37° C. | 1 | +++ | +++ | Cut | +++ | +++ | +++ | +++ |
| | 50° C. | 1 | + | + | Partial | ++ | ++ | + | + |
| | 25° C. | 8 | + | + | Partial | + | + | + | + |
| | 37° C. | 8 | − | − | No cut | − | − | − | − |
| | 50° C. | 8 | − | − | No cut | − | − | − | − |
| | 4° C. | 15 | + | + | Partial | + | + | + | + |
| | 25° C. | 15 | − | − | No cut | − | − | − | − |
| | 37° C. | 15 | − | − | No cut | − | − | − | − |
| | 4° C. | 30 | + | + | Partial | + | + | + | + |
| | 25° C. | 30 | − | − | No cut | − | − | − | − |
| | 4° C. | 60 | − | − | No cut | − | − | − | − |
| Raffinose + betaine + glycogen | 37° C. | 1 | +++ | +++ | Cut | +++ | +++ | +++ | +++ |
| | 50° C. | 1 | + | + | Partial | + | + | + | + |
| | 25° C. | 8 | ++ | ++ | Cut | ++ | ++ | + | ++ |
| | 37° C. | 8 | − | − | No cut | − | − | − | − |
| | 50° C. | 8 | − | − | No cut | − | − | − | − |
| | 4° C. | 15 | + | + | Partial | + | + | + | + |
| | 25° C. | 15 | − | − | No cut | − | − | − | − |
| | 37° C. | 15 | − | − | No cut | − | − | − | − |
| | 4° C. | 30 | + | + | Partial | − | − | + | + |
| | 25° C. | 30 | − | − | No cut | − | − | − | − |
| | 4° C. | 60 | − | − | No cut | − | − | − | − |
| Trehalose | 37° C. | 1 | +++ | +++ | Cut | +++ | +++ | +++ | +++ |
| | 50° C. | 1 | ++ | ++ | Cut | + | ++ | ++ | ++ |
| | 25° C. | 8 | + | + | Partial | + | + | + | + |
| | 37° C. | 8 | − | − | No cut | − | − | − | − |
| | 50° C. | 8 | − | − | No cut | − | − | − | − |
| | 4° C. | 15 | ++ | ++ | Cut | ++ | ++ | + | + |
| | 25° C. | 15 | + | + | Partial | + | + | + | + |
| | 37° C. | 15 | − | − | No cut | − | − | − | − |
| | 4° C. | 30 | + | + | Partial | + | + | + | + |
| | 25° C. | 30 | − | − | No cut | − | − | − | − |
| | 4° C. | 60 | + | + | Partial | − | − | − | − |
| Sorbitol | 37° C. | 1 | ++ | ++ | Cut | ++ | + | ++ | ++ |
| | 50° C. | 1 | ++ | ++ | Partial | + | + | ++ | ++ |
| | 25° C. | 8 | + | + | Partial | + | + | + | ++ |
| | 37° C. | 8 | + | + | Partial | + | + | + | + |
| | 50° C. | 8 | − | − | No cut | − | − | − | − |
| | 4° C. | 15 | + | + | Partial | + | + | + | + |
| | 25° C. | 15 | − | − | No cut | − | − | − | − |
| | 37° C. | 15 | − | − | No cut | − | − | − | − |
| | 4° C. | 30 | − | − | No cut | − | − | − | − |
| | 25° C. | 30 | − | − | No cut | − | − | − | − |
| | 4° C. | 60 | − | − | No cut | − | − | − | − |

EXAMPLE VIII

Compartmentalizing Sequential Reactions by Means of Using Mixed Phase Reaction Systems The thermostable reverse transcriptase enzyme used in this example, as in Example II, was a *Thermus thermophilus* recombinant DNA polymerase with enhanced reverse transcriptase activity with regard to the enzyme indicated in Example I, expressed in *Escherichia coli*, property of Biotools B&M Labs, S.A. (Spain), and purified by means of a non-chromatographic method developed by the same company (RETROTOOLS™ cDNA/DNA Polymerase). Said enzyme exhibits reverse transcriptase activity in the presence of $Mn^{2+}$ ions and DNA polymerase activity in the presence of $Mg^{2+}$ ions, both reactions being exclusive in conventional conditions. After purification, the enzyme was stored at −20° C. in a storage buffer containing 30 mM Tris HCl, pH 8, 25 mM glucose, 0.5 mM PMSF, 0.25% TWEEN™ 20 surfactant and 0.25% NP40™ surfactant.

A reaction buffer containing 1.5 mM EGTA and 4 mM $MgCl_2$ was prepared for carrying out the PCR reaction. 10 μl of the previously described mixture was added to each 0.2 ml tube, and the stabilizing mixtures that demonstrated better activity in the previous experiments (Examples I-VII) were added: melezitose or palatinitol in conjunction with lysine or glycogen or acacia gum, or raffinose with betaine and glycogen. The tubes thus prepared were dried in an Eppendorf 5301 centrifugal evaporator at temperatures comprised between 10° C. and 60° C. for a time period comprised between 30 and 120 minutes. The previously mentioned temperatures and times vary according to the stabilizing mixture used. After drying, the tubes were conserved at the temperatures indicated in Table 1. Their activity was assayed after the conservation periods indicated in said Table 1.

Lastly, a reaction buffer for carrying out the reverse transcription was prepared, containing 75 mM Tris HCl, pH 8, 200 mM $(NH_4)_2SO_4$, 0.01% TWEEN™ 20 surfactant, 1.5 mM $MnCl_2$, 0.125 mM of each dNTP (dATP, dCTP, dGTP and dTTP), 5 units of Tth DNA polymerase (RETRO- TOOLS™ cDNA/DNA polymerase) and 20 picomoles of each one of the II-1 and II-2 primers (described in Example II) which amplify a fragment of 1,122 by of the mRNA from the CD8α mouse gene.

For the activity assay, 15 µl of the reverse transcription reaction mixture and 100 ng of mouse RNA were added to all the 0.2 ml tubes in which the PCR mixture had been dried, adjusting the final volume with $H_2O$ up to 20 µl. In half the tubes, the gelled content of the tube was re-suspended by means of pipetting, whereas it was not re-suspended in the other half. As a control, a two-step RT-PCR reaction was included in all the experiments, in the conditions described in Example II, wherein no stabilizing mixture had been included.

All the tubes were subjected to a single-step round of reverse transcription-amplification, and without the inclusion of reagents during the process. Said reaction consisted of incubating at 94° C. for 1 minute followed by incubating at 60° C. for 30 minutes. Then, the tubes were subjected to a high temperature so as to permit the release of the reagents included in the non-re-suspended gelled mixtures, consisting of incubation at 83° C. for 5 minutes followed by incubation at 94° C. for 3 minutes. Finally, 40 repeated cycles were carried out, each one of which had a denaturation step at 94° C. for 45 seconds, a hybridization step at 55° C. for 30 seconds and an elongation step at 72° C. for 1 minute. Once the 40 amplification cycles were finished, a final elongation step was carried out at 72° C. for 7 minutes. The amplification reaction was carried out in an Eppendorf MASTERCYCLER™ thermal cycler.

The amplified products were analyzed by means of electrophoresis in 1% agarose gel (weight/volume), finding a single, 1,122 bp amplification band in all those cases in which the reaction was positive. The activity of the assayed reaction mixtures was determined by means of densitometry of the resulting amplification bands, using for this a TDI GEL-PRINTER™ image analyzer, using the GELSUPER™ computer program also developed by TDI.

The activity analysis of the amplification reactions demonstrated that the reaction was inhibited in all those tubes in which the gelled mixture was re-suspended by pipetting prior to carrying out the reverse transcription reaction, thus bringing into contact $MnCl_2$, EGTA and $MgCl_2$. On the contrary, in the tubes in which the gelled mixture was not re-suspended, positive results were obtained with an intensity similar to that obtained in the two-step reverse transcription and amplification reactions. This fact demonstrates that the $MgCl_2$ and EGTA gelled mixture had been kept compartmentalized, until being released by incubation at high temperatures, permitting sequencing two reactions that are exclusive to one another.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A process for preparing a stabilized and partially dried enzyme composition, comprising:
   a) bringing into contact in a single container:
      i) an aqueous reaction mixture comprising at least one enzyme for an enzymatic reaction and all or part of the reagents which are necessary for carrying out said enzymatic reaction; and
      ii) an aqueous stabilizing mixture comprising:
         at least one protective agent against drying selected from the group consisting of melezitose and raffinose;
         at least one inhibitor of a condensation reaction between carbonyl or carboxyl groups and amine or phosphate groups selected from the group consisting of betaine and lysine; and
         at least one inert polymer capable of generating a mesh structure preventing the mobility of the dried reagents which is glycogen;
      to produce a liquid phase aqueous mixture comprising said reaction mixture and said stabilizing mixture; and
   b) subjecting said liquid phase aqueous mixture to a temperature of 10° C. to 60° C., at a pressure lower than atmospheric pressure, to produce a stabilized and partially dried enzyme composition having a moisture content of between 1% and 30%.

2. The process of claim 1, wherein said at least one enzyme is selected from the group consisting of thermostable RNA amplification enzymes; thermostable DNA amplification enzymes; thermolabile RNA amplification enzymes; thermolabile DNA amplification enzymes; restriction enzymes; enzymes intervening in nucleic acid amplification, sequencing, or characterization reactions; and mixtures thereof.

3. The process of claim 1, wherein said reaction mixture comprises an enzyme selected from the group consisting of thermostable RNA amplification enzymes; thermostable DNA amplification enzymes; thermolabile RNA amplification enzymes; thermolabile DNA amplification enzymes; restriction enzymes; enzymes intervening in nucleic acid amplification, sequencing, or characterization reactions; and mixtures thereof, together with all the reagents which are necessary for carrying out an enzymatic reaction in which said enzyme is involved.

4. The process of claim 1, wherein said container is a reaction tube or a well of a multi-well plate.

5. The process of claim 1, wherein said stabilizing mixture further comprises glycerol.

6. The process of claim 1, wherein the stabilized and partially dried enzyme composition has a moisture content of between 1% and 20%.

7. The process of claim 1, wherein said reaction mixture comprises at least one enzyme for an enzymatic reaction and all of the reagents which are necessary for carrying out said enzymatic reaction.

8. A stabilized and partially dried enzyme composition, produced by subjecting a liquid phase aqueous mixture to a temperature of 10° C. to 60° C., at a pressure lower than atmospheric pressure,
   wherein said liquid phase aqueous mixture comprises at least one enzyme and a stabilizing mixture comprising (i) at least one protective agent against drying which is melezitose or raffinose, (ii) at least one inhibitor of the condensation reaction between carbonyl or carboxyl groups and amine or phosphate groups which is betaine or lysine, and (iii) at least one inert polymer capable of generating a mesh structure preventing the mobility of the dried reagents which is glycogen,
   and wherein said stabilized and partially dried enzyme composition has a moisture content of between 1% and 30%.

9. The stabilized and partially dried enzyme composition of claim 8, having a moisture content of between 1% and 20%.

10. The stabilized and partially dried enzyme composition of claim 8, wherein said at least one enzyme is selected from the group consisting of thermostable RNA amplification enzymes; thermostable DNA amplification enzymes; thermolabile RNA amplification enzymes; thermolabile DNA amplification enzymes; restriction enzymes; enzymes intervening in nucleic acid amplification, sequencing, or characterization reactions; and mixtures thereof.

11. The stabilized and partially dried enzyme composition of claim 8, wherein said at least one enzyme is selected from the group consisting of thermostable RNA amplification enzymes; thermostable DNA amplification enzymes; thermolabile RNA amplification enzymes; thermolabile DNA amplification enzymes; restriction enzymes; enzymes intervening in nucleic acid amplification, sequencing, or characterization reactions; and mixtures thereof, together with all or part of the reagents which are necessary for carrying out an enzymatic reaction in which said enzyme is involved.

12. The stabilized and partially dried enzyme composition of claim 11, wherein said reagents are selected from the group consisting of cofactors; enzyme substrates; additives enhancing or modulating the enzymatic reactions; dNTPs; ddNTPs; optionally labeled oligonucleotide primers and probes; and mixtures thereof.

13. The stabilized and partially dried enzyme composition of claim 8, wherein the enzyme is one of a DNA polymerase enzyme, a thermostable reverse transcriptase enzyme or a non-thermostable reverse transcriptase enzyme, and wherein the composition optionally further comprises one or more of a labeled deoxynucleotide triphosphate, cofactors which are necessary for enzymatic activity or additives enhancing or modulating said enzymatic activity.

14. The stabilized and partially dried enzyme composition of claim 13, further comprising at least one of i) optionally labeled oligonucleotide reaction primers, necessary for the specific amplification of a target nucleotide sequence, and ii) optionally labeled oligonucleotide probes, necessary for carrying out a hybridization assay, optionally together with any additive or coadjuvant of the hybridization reaction.

15. The stabilized and partially dried enzyme composition of claim 8, further comprising dideoxyribonucleotides (ddNTPs).

16. The stabilized and partially dried enzyme composition of claim 8, wherein said at least one enzyme is a restriction enzyme, optionally together with all the cofactors and additives which are necessary for carrying out a restriction analysis.

17. The stabilized and partially dried enzyme composition of claim 8, presented in a ready-to-use format.

18. The stabilized and partially dried enzyme composition of claim 8, wherein said stabilizing mixture further comprises glycerol.

19. A kit comprising the stabilized and partially dried enzyme composition of claim 8.

\* \* \* \* \*